(12) United States Patent
Liang et al.

(10) Patent No.: US 11,576,894 B2
(45) Date of Patent: Feb. 14, 2023

(54) COMBINATION THERAPY FOR THE TREATMENT OF DIABETES

(71) Applicant: Janssen Pharmaceutica N.V., Beerse (BE)

(72) Inventors: Yin Liang, Ambler, PA (US); John Ryan, Chalfont, PA (US); Abraham B. Woldu, Souderton, PA (US); Lisa Wu, Merion Station, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/413,480

(22) Filed: Jan. 24, 2017

(65) Prior Publication Data

US 2017/0128414 A1    May 11, 2017

Related U.S. Application Data

(63) Continuation of application No. 14/964,670, filed on Dec. 10, 2015, now abandoned, which is a continuation of application No. 14/452,884, filed on Aug. 6, 2014, now abandoned, which is a continuation of application No. 12/830,479, filed on Jul. 6, 2010, now abandoned.

(60) Provisional application No. 61/223,881, filed on Jul. 8, 2009.

(51) Int. Cl.

| A61K 31/7034 | (2006.01) |
|---|---|
| A61K 31/7042 | (2006.01) |
| A61K 31/155 | (2006.01) |
| A61K 31/381 | (2006.01) |
| A61K 47/38 | (2006.01) |
| A61K 31/4436 | (2006.01) |

(52) U.S. Cl.
CPC .......... *A61K 31/381* (2013.01); *A61K 31/155* (2013.01); *A61K 31/4436* (2013.01); *A61K 31/7034* (2013.01); *A61K 31/7042* (2013.01); *A61K 47/38* (2013.01)

(58) Field of Classification Search
None
See application file for complete search history.

(56) References Cited

U.S. PATENT DOCUMENTS

| 2,799,241 A | 7/1949 | Wurster |
|---|---|---|
| 4,160,861 A | 7/1979 | Cole et al. |
| 4,584,369 A | 4/1986 | Klein et al. |
| 5,149,838 A | 9/1992 | Humphrey et al. |
| 5,292,461 A | 3/1994 | Juch et al. |
| 5,401,435 A | 3/1995 | Burzio et al. |
| 5,424,406 A | 6/1995 | Tsujihara et al. |
| 5,610,294 A | 3/1997 | Lam et al. |
| 5,731,292 A | 3/1998 | Tsujihara et al. |
| 5,767,094 A | 6/1998 | Tsujihara et al. |
| 5,780,483 A | 7/1998 | Widdowson et al. |
| 5,830,873 A | 11/1998 | Tsujihara et al. |
| 5,861,385 A | 1/1999 | Angerbauer et al. |
| 5,945,533 A | 8/1999 | Kometani et al. |
| 6,048,842 A | 4/2000 | Tsujihara et al. |
| 6,069,238 A | 5/2000 | Hitchcock et al. |
| 6,153,632 A | 11/2000 | Rieveley |
| 6,277,833 B1 | 8/2001 | Angerbauer et al. |
| 6,297,363 B1 | 10/2001 | Kubo et al. |
| 6,414,126 B1 * | 7/2002 | Ellsworth .............. A61K 31/70 536/1.11 |
| 6,420,513 B2 | 7/2002 | Minami |
| 6,448,415 B1 | 9/2002 | Lee et al. |
| 6,475,521 B1 | 11/2002 | Timmins et al. |
| 6,479,661 B1 | 11/2002 | Buchholz et al. |
| 6,515,117 B2 | 2/2003 | Ellsworth et al. |
| 6,562,791 B1 | 5/2003 | Maurya et al. |
| 6,617,313 B1 | 9/2003 | Maurya et al. |
| 6,627,611 B2 | 9/2003 | Tomiyama et al. |
| 6,800,761 B1 | 10/2004 | Franc et al. |
| 7,008,959 B2 | 3/2006 | Franc et al. |
| 7,045,665 B2 | 5/2006 | Fujikura et al. |
| 7,074,826 B2 | 7/2006 | Wechter et al. |
| 7,084,123 B2 | 8/2006 | Fujikura et al. |
| 7,157,584 B2 * | 1/2007 | Kuroita ................ C07D 413/14 548/132 |
| 7,202,350 B2 | 4/2007 | Imamura et al. |
| 7,271,153 B2 | 9/2007 | Nishimura et al. |
| 7,288,528 B2 | 10/2007 | Frick et al. |
| 7,294,618 B2 | 11/2007 | Fushimi et al. |
| 7,375,213 B2 | 5/2008 | Deshpande et al. |
| 7,417,032 B2 | 8/2008 | Eckhardt et al. |

(Continued)

FOREIGN PATENT DOCUMENTS

| CA | 2494177 A1 | 2/2004 |
|---|---|---|
| CN | 101057835 A | 10/2007 |

(Continued)

OTHER PUBLICATIONS

Adachi et al., "T-1095, a Renal Na+-Glucose Transporter Inhibitor, Improves Hyperglycemia in Streptozotocin-Induced Diabetic Rats.", *Metabolism*, Aug. 2000, pp. 990-995, vol. 49(8).

(Continued)

*Primary Examiner* — Traviss C McIntosh, III

(57) ABSTRACT

The present invention is directed to co-therapy and methods for the treatment and prevention of glucose-related disorders such as Type 2 diabetes mellitus and Syndrome X. The present invention is further directed to pharmaceutical compositions for the co-therapy and methods described herein.

12 Claims, No Drawings

(56) References Cited

U.S. PATENT DOCUMENTS

| | | |
|---|---|---|
| 7,511,022 B2 | 3/2009 | Beavers et al. |
| 7,566,699 B2 | 7/2009 | Fushimi et al. |
| 7,576,064 B2 | 8/2009 | Kikuchi et al. |
| 7,666,845 B2 | 2/2010 | Cook et al. |
| 7,932,379 B2 | 4/2011 | Deshpande et al. |
| 7,943,582 B2 * | 5/2011 | Nomura .................. C07H 7/04 514/23 |
| 7,943,788 B2 | 5/2011 | Nomura et al. |
| 8,222,219 B2 | 7/2012 | Nomura et al. |
| 8,513,202 B2 | 8/2013 | Nomura et al. |
| 8,785,403 B2 | 7/2014 | Nomura et al. |
| 2001/0041674 A1 | 11/2001 | Tomiyama et al. |
| 2002/0032164 A1 | 3/2002 | Dale et al. |
| 2002/0052326 A1 | 5/2002 | Washburn |
| 2002/0111315 A1 | 8/2002 | Washburn et al. |
| 2002/0177602 A1 | 11/2002 | Piper et al. |
| 2002/0183345 A1 | 12/2002 | Piper et al. |
| 2003/0024914 A1 | 2/2003 | Aleshin |
| 2003/0064935 A1 | 4/2003 | Gougoutas |
| 2003/0087843 A1 | 5/2003 | Washburn |
| 2003/0114390 A1 | 6/2003 | Washburn et al. |
| 2003/0191121 A1 | 10/2003 | Miller et al. |
| 2004/0053855 A1 | 3/2004 | Fujikura et al. |
| 2004/0063646 A1 | 4/2004 | Fujikura et al. |
| 2004/0110936 A1 | 6/2004 | Ohsumi et al. |
| 2004/0116357 A1 | 6/2004 | Fushimi et al. |
| 2004/0132669 A1 | 7/2004 | Nishimura et al. |
| 2004/0138143 A1 | 7/2004 | Glombik et al. |
| 2004/0259819 A1 | 12/2004 | Frick et al. |
| 2005/0014704 A1 | 1/2005 | Frick et al. |
| 2005/0032711 A1 | 2/2005 | Patel et al. |
| 2005/0032712 A1 | 2/2005 | Urbanski |
| 2005/0037980 A1 | 2/2005 | Rybczynski et al. |
| 2005/0037981 A1 | 2/2005 | Beavers et al. |
| 2005/0049203 A1 | 3/2005 | Nishimura et al. |
| 2005/0124555 A1 | 6/2005 | Tomiyama et al. |
| 2005/0124556 A1 | 6/2005 | Burton |
| 2005/0209166 A1 | 9/2005 | Eckhardt et al. |
| 2005/0233988 A1 | 10/2005 | Nomura et al. |
| 2005/0256317 A1 | 11/2005 | Sato et al. |
| 2005/0287207 A1 | 12/2005 | Koike et al. |
| 2006/0009400 A1 | 1/2006 | Eckhardt et al. |
| 2006/0035841 A1 | 2/2006 | Eckhardt et al. |
| 2006/0122126 A1 | 6/2006 | Imamura et al. |
| 2006/0141023 A1 | 6/2006 | Trehan et al. |
| 2006/0189548 A1 | 8/2006 | Himmelsbach et al. |
| 2006/0217323 A1 | 9/2006 | Patel et al. |
| 2006/0229260 A1 | 10/2006 | Rybczynski et al. |
| 2006/0234954 A1 | 10/2006 | Urbanski |
| 2006/0247179 A1 | 11/2006 | Fushimi et al. |
| 2006/0258749 A1 | 11/2006 | Eckhardt et al. |
| 2006/0293251 A1 | 12/2006 | Urbanski et al. |
| 2007/0027092 A1 | 2/2007 | Himmelsbach et al. |
| 2007/0049537 A1 | 3/2007 | Eckhardt et al. |
| 2007/0060531 A1 | 3/2007 | Kikuchi et al. |
| 2007/0060545 A1 | 3/2007 | Nomura et al. |
| 2007/0299033 A1 | 12/2007 | McMahon et al. |
| 2008/0027122 A1 | 1/2008 | Nomura et al. |
| 2008/0119422 A1 | 5/2008 | Nomura et al. |
| 2008/0132563 A1 | 6/2008 | Kakinuma et al. |
| 2008/0146515 A1 | 6/2008 | Nomura et al. |
| 2008/0234366 A1 | 9/2008 | Bindra et al. |
| 2009/0124702 A1 | 5/2009 | Siva Satya Krishna Babu et al. |
| 2009/0143316 A1 | 6/2009 | Imamura et al. |
| 2009/0233874 A1 | 9/2009 | Abdel-Magid et al. |
| 2010/0063141 A1 | 3/2010 | Seed et al. |
| 2010/0099883 A1 | 4/2010 | Filliers et al. |
| 2010/0331999 A1 | 12/2010 | Arron |
| 2011/0009347 A1 | 1/2011 | Liang et al. |
| 2011/0065658 A1 | 3/2011 | Leslie |
| 2011/0087017 A1 | 4/2011 | Farina et al. |
| 2011/0171159 A1 | 7/2011 | Berbemitz et al. |
| 2011/0212905 A1 | 9/2011 | Nomura et al. |
| 2011/0263493 A1 | 10/2011 | Dugi et al. |
| 2012/0058941 A1 | 3/2012 | Nomura et al. |
| 2012/0115799 A1 | 5/2012 | Wang et al. |
| 2012/0165410 A1 | 6/2012 | Dodd et al. |
| 2014/0243262 A1 | 8/2014 | Bindra et al. |

FOREIGN PATENT DOCUMENTS

| | | |
|---|---|---|
| EP | 0355750 A1 | 2/1990 |
| EP | 0348184 B1 | 3/1993 |
| EP | 0579204 A2 | 1/1994 |
| EP | 0579204 A3 | 1/1994 |
| EP | 0625513 B1 | 9/1999 |
| EP | 1172362 A1 | 1/2002 |
| EP | 1338603 A1 | 8/2003 |
| EP | 1435240 A2 | 7/2004 |
| EP | 1528066 A1 | 5/2005 |
| EP | 1845095 | 10/2007 |
| EP | 1229918 B1 | 3/2008 |
| EP | 1956023 A1 | 3/2008 |
| GB | 2359554 | 8/2001 |
| GB | 2399015 A | 9/2004 |
| JP | 59039889 A | 3/1984 |
| JP | 63-233975 A | 9/1988 |
| JP | H03-503280 | 7/1991 |
| JP | 4-253974 A | 9/1992 |
| JP | 06256354 A | 9/1994 |
| JP | 07242526 A | 9/1995 |
| JP | 9-263549 A | 10/1997 |
| JP | 2000-34230 A | 2/2000 |
| JP | 2000-34239 A | 2/2000 |
| JP | 2001-288178 A | 10/2001 |
| JP | 2002167430 A | 6/2002 |
| JP | 2003-012686 A1 | 1/2003 |
| JP | 2003238417 A | 8/2003 |
| JP | 2003313168 A | 11/2003 |
| JP | 2007-230999 A | 9/2007 |
| JP | 2008-280345 A | 11/2008 |
| WO | WO 1989/05639 A1 | 6/1989 |
| WO | WO 1993/09100 A1 | 5/1993 |
| WO | WO 1993/21178 A1 | 10/1993 |
| WO | WO 1994/14807 A1 | 7/1994 |
| WO | WO 1996/13258 A1 | 5/1996 |
| WO | WO 1996/31234 A1 | 10/1996 |
| WO | WO 1997/17949 A1 | 5/1997 |
| WO | WO 1997/25033 A1 | 7/1997 |
| WO | WO 1998/42347 A1 | 10/1998 |
| WO | WO 1999/061026 A1 | 12/1999 |
| WO | WO 1999/065861 A1 | 12/1999 |
| WO | WO 1999/67236 A | 12/1999 |
| WO | WO 2000/27823 A1 | 5/2000 |
| WO | WO 2000/28989 A1 | 5/2000 |
| WO | WO 2000/74681 A1 | 12/2000 |
| WO | WO 2001/127128 | 4/2001 |
| WO | WO 2001/032157 A2 | 5/2001 |
| WO | WO 2001/32158 A2 | 5/2001 |
| WO | WO 2001/64669 A1 | 9/2001 |
| WO | WO 2001/68660 A1 | 9/2001 |
| WO | WO 2001/74834 A1 | 10/2001 |
| WO | WO 2001/74835 A1 | 10/2001 |
| WO | WO 2001/085167 A1 | 11/2001 |
| WO | WO 2002/026706 A2 | 4/2002 |
| WO | WO 2002/053573 A1 | 7/2002 |
| WO | WO 2002/068439 A1 | 9/2002 |
| WO | WO 2002/068440 A1 | 9/2002 |
| WO | WO 2002/070020 A2 | 9/2002 |
| WO | WO 2002/070020 A3 | 9/2002 |
| WO | WO 2002/083066 A2 | 10/2002 |
| WO | WO 2002/088157 A1 | 11/2002 |
| WO | WO 2002/094262 A1 | 11/2002 |
| WO | WO 2002/096357 A2 | 12/2002 |
| WO | WO 2003/000712 A1 | 1/2003 |
| WO | WO 2003/011880 A1 | 2/2003 |
| WO | WO 2003/020737 A1 | 3/2003 |
| WO | WO 2003/040121 A1 | 5/2003 |
| WO | WO 2003/043621 A1 | 5/2003 |
| WO | WO 2003/087104 A1 | 10/2003 |
| WO | WO 2003/099836 A1 | 12/2003 |
| WO | WO 2003/105809 A1 | 12/2003 |
| WO | WO 2004/007517 A1 | 1/2004 |
| WO | WO 2004/013118 A1 | 2/2004 |

(56) References Cited

FOREIGN PATENT DOCUMENTS

| | | |
|---|---|---|
| WO | WO 2004/014931 A1 | 2/2004 |
| WO | WO 2004/019958 A1 | 3/2004 |
| WO | WO 2004/052902 A1 | 6/2004 |
| WO | WO 2004/052903 A1 | 6/2004 |
| WO | WO 2004/063209 A2 | 7/2004 |
| WO | WO 2004/063209 A3 | 7/2004 |
| WO | WO 2004/064806 A | 8/2004 |
| WO | WO 2004/076470 A2 | 9/2004 |
| WO | WO 2004/080990 A1 | 9/2004 |
| WO | WO 2004/087727 A1 | 10/2004 |
| WO | WO 2004/099230 A1 | 11/2004 |
| WO | WO 2004/113359 A1 | 12/2004 |
| WO | WO 2005/009539 A2 | 2/2005 |
| WO | WO 2005/009954 A2 | 2/2005 |
| WO | WO 2005/012326 A1 | 2/2005 |
| WO | WO 2005/058845 A2 | 6/2005 |
| WO | WO 2005/070396 A1 | 8/2005 |
| WO | WO 2006/007448 A2 | 1/2006 |
| WO | WO 2006/010557 | 2/2006 |
| WO | WO 2006/080577 A1 | 8/2006 |
| WO | WO 2006/108842 A1 | 10/2006 |
| WO | WO 2007/025943 A2 | 3/2007 |
| WO | WO 2007/031548 A2 | 3/2007 |
| WO | WO 2007/087441 A2 | 8/2007 |
| WO | WO 2008/002824 A1 | 1/2008 |
| WO | WO 2008/013322 A1 | 1/2008 |
| WO | WO 2008/020011 A1 | 2/2008 |
| WO | WO 2008/034859 A1 | 3/2008 |
| WO | WO 2008/050987 A1 | 5/2008 |
| WO | WO 2008/055870 A1 | 5/2008 |
| WO | WO 2008/055940 A2 | 5/2008 |
| WO | WO 2008/069327 A1 | 6/2008 |
| WO | WO 2008/070609 A1 | 6/2008 |
| WO | WO 2008/113000 A1 | 9/2008 |
| WO | WO 2008/136392 A1 | 11/2008 |
| WO | WO 2009/022010 A1 | 2/2009 |
| WO | WO 2009/026537 | 2/2009 |
| WO | WO 2009/035969 A1 | 3/2009 |
| WO | WO 2009/091082 A1 | 7/2009 |
| WO | WO 2009/121945 A2 | 10/2009 |
| WO | WO 2009/125975 A2 | 10/2009 |
| WO | WO 2009/0143020 A1 | 11/2009 |
| WO | WO 2010/009243 A1 | 1/2010 |
| WO | WO 2010/022313 A2 | 2/2010 |
| WO | WO 2010/043682 A2 | 4/2010 |
| WO | WO 2010/045656 A2 | 4/2010 |
| WO | WO 2010/065069 A2 | 6/2010 |
| WO | WO 2010/092125 A1 | 8/2010 |
| WO | WO 2011/047113 A1 | 4/2011 |
| WO | WO 2011/048112 A1 | 4/2011 |
| WO | WO 2011/120923 A1 | 10/2011 |
| WO | WO 2011/142478 A1 | 11/2011 |
| WO | WO 2011/143296 A1 | 11/2011 |
| WO | WO 2012/006298 A2 | 1/2012 |

OTHER PUBLICATIONS

Ahmad et al., "Synthesis and Structure Determination of Some Oxadiazole-2-Thione and Triazole-3-Thione Galactosides.", *Nucleosides, Nucleotides & Nucleic Acids*, 2001, pp. 1671-1682, vol. 20(9).
Albertoni Borghese et al., "Inhibitors of sodium/glucose cotransport.", *Drugs of the Future*, Apr. 2009, pp. 297-305, vol. 34(4), Prous Science, XP007915342.
Amishiro et al., "Synthesis and Antitumor Activity of Duocarmycin Derivatives: A-Ring Pyrrole Compounds Bearing 5-Membered Heteroarylacryloyl Groups.", *Chem. Pharm. Bull.*, Oct. 1999, pp. 1393-1403, vol. 47(10).
Appleton et al., "A Mild and Selective C-3 Reductive Alkylation of Indoles.", *Tetrahedron Letters*, 1993, pp. 1529-1532, vol. 34(9).
Apsel et al., "General Entries to C-aryl glycosides. Formal synthesis of galtamycinone.", *Tetrahedron Letters*, 2003, pp. 1075-1077, vol. 44.

Arakawa et al., "Improved diabetic syndrome in C57BL/KsJ-db/db Mice by Oral Administration of the Na+-Glucose Cotransporter Inhibitor T-1095.", *British Journal of Pharmacology*, 2001, pp. 578-586, vol. 132.
Banker, *Modern Pharmaceutics*, Third Edition, Marcel Dekker, Inc., published 1996, p. 596.
Beck-Nielsen et al., "In Vivo Glucose Metabolism, Insulin Secretion and, Insulin Action in Europids with non-insulin-dependent Diabetes mellitus (NIDDM) and Their First-degree Relatives.", *Diabetic Medicine*, Sep. 1996, pp. S78-S84, vol. 13(9 Supp. 6).
Benhaddou et al.,"Tetra-n-propylammonium tetra-oxoruthenate(VII): a reagent of choice for the oxidation of diversely protected glycopyranoses and glycofuranoses to lactones.", *Carbohydrate Research*, 1994, pp. 243-250, vol. 260.
Bertolini et al., "A New Simple One-Pot Regioselective Preparation of Mixed Diesters of Carbonic Acid.", *Journal of Organic Chemistry*, 1998, pp. 6031-6034, vol. 63(17).
Blair et al., "Effect of Ring Fluorination on the Pharmacology of Hallucinogenic Tryptamines.", *J. Med. Chem.*, 2000, pp. 4701-4710, vol. 43.
Boehm et al., "Novel Inhibitors of DNA Gyrase: 3D Structure Based Biased Needle Screening, Hit Validation by Biophysical Methods, and 3D Guided Optimization. A Promising Alternative to Random Screening.", *J. Med. Chem.*, 2000, pp. 2664-2674, vol. 43(14).
Bookser, B.C., "2-Benzyloxymethy1-5-(tributylstannyptetrazole. A reagent for the preparation of 5-aryl- and 5-heteroaryl-1H-tetrazoles via the Stille reaction.", *Tetrahedron Letters*, 2000, 2805-2809, vol. 41.
Bouillon et al., "Synthesis of novel halopyridinylboronic acids and esters. Part 2: 2,4, or 5-Halopyridin-3-yl-boronic acids and esters.", *Tetrahedron*, 2002, pp. 3323-3328, vol. 58.
Bouillon et al., "Synthesis of novel halopyridinylboronic acids and esters. Part 3: 2, or 3-Halopyridin-4-yl-boronic acids and esters.", *Tetrahedron*, 2002, pp. 4369-4373, vol. 58.
Bouillon et al., "Synthesis of novel halopyridinylboronic acids and esters. Part 4: Halopyridin-2-yl-boronic acids and esters are stable, crystalline partners for classical Suzuki cross-coupling.", *Tetrahedron*, 2003, pp. 10043-10049, vol. 59.
Braga et al., "Making crystals from crystals: a green route to crystal engineering and polymorphism.", *Chem. Commun.*, 2005, pp. 3635-3645.
Brooks et al., "Boron Trichloride/Tetra-n-Butylammonium Iodide: A Mild, Selective Combination Reagent for the Cleavage of Primary Alkyl Aryl Ethers.", *J. Org. Chem.*, 1999, pp. 9719-9721, vol. 64.
Brooks et al., "Dapagliflozin for the Treatment of Type 2 Diabetes.", *The Annals of Pharmacotherapy*, 2009, pp. 1286-1293, vol. 43.
CAS Reg. No. 487001-40-1, IP Organisers, Entered STN Feb. 7, 2003, pp. 1-2.
Caumo et al., "Insulin Sensitivity from Meal Tolerance Tests in Normal Subjects: A Minimal Model Index.", *J. of Clinical Endocrinology & Metabolism*, 2000, pp. 4396-4402, vol. 85(11).
Cicchillo et al., "A convenient synthesis of glycosyl chlorides from sugar hemiacetals using triphosgene as the chlorine source.", *Carbohydrate Research*, 2000, pp. 431-434, vol. 328.
Clayden et al., "Dearomatizing Cyclization of Arylsulfonylalkoxymethyl Lithiums: A Route to the Podophyllotoxin Skeleton.", *Organic Letters*, 2003, pp. 831-834, vol. 5(6).
Clinical Trial NTC00707954, ClinicalTrials.gov/archive/NTC00707954/2008_06_30, View of Trial on Jun. 30, 2008.
Comins et al., "Synthesis of 3-Substituted Indoles via N-Acylindolium Ions.", *Tetrahedron Letters*, 1986, pp. 1869-1872, vol. 27(17).
Cottet et al., "Recommendable Routes to Trifluoromethyl-Substituted Pyridine—and Quinolinecarboxylic Acids.", *Eur. J. Org. Chem.*, 2003, pp. 1559-1568.
Czernecki et al., "C-Glycosides. 7. Stereospecific C-Glycosylation of Aromatic and Heterocyclic Rings.", *J. Org. Chem.*, 1989, pp. 610-612, vol. 54.
De Las Heras et al., "Alkylating Nucleosides 1. Synthesis and Cytostatic Activity of N-Glycosyl(halomethyl)-1,2,3-triazoles. A New Type of Alkylating Agent.", *Journal of Medicinal Chemistry*, 1979,pp. 496-501, vol. 22(5).
Deeg et al., "Pioglitazone and Rosiglitazone Have Different Effects on Serum Lipoprotein Particle Concentrations and Sizes in Patients

(56) References Cited

OTHER PUBLICATIONS

With Type 2 Diabetes and Dyslipidemia.", *Diabetes Care*, Oct. 2007, pp. 2458-2464, vol. 30(10).
Deetjen et al., "Renal Handling of D-Glucose and Other Sugars.", *Textbook of Nephrology*, 3rd Edition, 1995, pp. 90-94. vol. 1.
Devivar et al., "Benzimidazole Ribonucleosides: Design, Synthesis, and Antiviral Activity of Certain 2-(Alkylthio)- and 2-(Benzylthio)-5,6-dichloro-1-(.beta.-D-ribofuranosyl)benzimidazolesl.", *J.Med. Chem.*, 1994, pp. 2942-2949, vol. 37.
Dewynter et al., "Synthesis of Pseudomucleosides containing Chiral Sulfahydantoins as Aglycone (II).", *Tetrahedron*, 1996, pp. 993-1004, vol. 52(3).
Dillard et al., "Indole Inhibitors of Human Nonpancreatic Secretory Phospholipase A2. 1. Indole-3-acetamides.", *J. Med. Chem.*, 1996, pp. 5119-5136, vol. 39.
Dinneen, S.F., "The Postprandial State: Mechanisms of Glucose Intolerance.", *Diabetic Medicine*, Aug. 1997, pp. S19-S24, vol. 14, Issue S3.
Dondoni et al., "Stereoselective synthesis of C-glycosylphosphonates from their ketols. Reconsideration of an abandoned route.", *Tetrahedron: Asymmetry*, 2000, pp. 305-317, vol. 11.
Dondoni et al., "Thiazole-Based Synthesis of Formyl C-Glycosides.", *J. Org. Chem.*, 1994, pp. 6404-6412, vol. 59.
Dudash et al., "Glycosylated dihydrochalcones as potent and selective sodium glucose co-transporter 2 (SGLT2) inhibitors.", *Bioorganic & Medicinal Chemistry Letters*, 2004, pp. 5121-2125, vol. 14.
Dunn et al., "Analgetic and antiinflammatory 7-Aroylbenzofuran-5-ylacetic acids and 7-Aroylbenzothiophene-5-ylacetic Acids.", *Journal of Med. Chem.*, 1986, pp. 2326-2329, vol. 29(1).
Eid et al., "Reaction of Some 1,2,4-Triazines with Acetobromoglucose.", *Arch. Pharm.* (Weinheim), 1990, pp. 243-245, vol. 323.
Ellsworth et al., "Aglycone exploration of C-arylglucoside inhibitors of renal sodium-dependent glucose transporter SGLT2.", *Bioorganic & Medicinal Chemistry Letters*, 2008, pp. 4770-4773, vol. 18.
Ellsworth et al., "C-Arylglucoside synthesis: triisopropylsilane as a selective reagent for the reduction of an anomeric C-phenyl ketal.", *Tetrahedron: Asymmetry*, 2003, pp. 3243-3247, vol. 14.
Emancipator, K., "Laboratory diagnosis and monitoring of diabetes mellitus.", *Am J Clin Pathol.*, Nov. 1999, pp. 65-674, vol. 112(5).
Frahn et al., "Functionalized AB-Type Monomers for Suzuki Polycondensation.", *Synthesis*, Nov. 1997, pp. 1301-1304.
Fresneda et al., "Synthesis of the indole alkaloids meridianins from the tunicate Aplidium meridianum.", *Tetrahedron*, 2001, pp. 2355-2363, vol. 57.
Fuller et al., "Thienothiophenes. Part 2. Synthesis, metallation and bromine-lithium exchange reactions of thieno[3,2-b-thiophene and its polybromo derivatives.", *J. Chem. Soc.*, Perkin Trans. 1., 1997, pp. 3465-3470.
Ganesh et al., "Synthesis and biological evaluation of fluorescently labeled epothilone analogs for tubulin binding studies.", *Tetrahedron*, 2003, pp. 9979-9984, vol. 59.
Gershell, L., "Type 2 diabetes market.", *Nature Reviews Drug Discovery*, May 2005, pp. 367-368, vol. 4.
Gohier et al., "ortho-Metalation of Unprotected 3-Bromo and 3-Chlorobenzoic Acids with Hindered Lithium Dialkylamides.", *J. Org. Chem.*, 2003, pp. 2030-2033, vol. 68.
Goldberg R.B., "Prevention of Type 2 Diabetes.", *Medical Clinics of North America*, Jul. 1998, pp. 805-821, vol. 82(4).
Gong, H., et al., "Diastereoselective Ni-Catalyzed negishi Cross Coupling Approach to Saturated, Fully Oxygenated C-Alkyl and C-Aryl Glycosides.", *Journal of the American Chemical Society*, Sep. 10, 2008, pp. 12177-12183, vol. 130(36), XP002612364.
Goodman & Gilman's the Pharmacological Basis of Therapeutics, 10th Edition, McGraw-Hill Medical Publishing Division, 2001, pp. 54-57.
Greene et al., "Protective Groups in Organic Synthesis.", 3rd Edition, 1999, pp. 116-121.
Greene et al., "Protective Groups in Organic Synthesis.", 3rd Edition, 1999, pp. 170.

Gronowitz et al., "Some Substitution Reactions of 1-(2-Thienyl)pyrazole and 1-(3'-Thienyl)pyrazole.", *Chemica Scripta.*, 1979, pp. 157-161, vol. 13.
Groop et al., "Characterization of the Prediabetic State.", *American Journal of Hypertension*, Sep. 1997, pp. 172S-180S, vol. 10(9Part2).
Gros et al., "Efficient and Regioselective Access to Bis-heterocycles via Palladium-Catalysed Coupling of Organostannanes and Organozincates Derived from C-6 Lithiated 2-Methoxypyridine.", *Synthesis*, 1999, pp. 754-756, No. 5.
Haffner S.M., "Impaired Glucose Tolerance, Insulin Resistance and Cardiovascular Disease.", *Diabetic Medicine*, Aug. 1997, pp. S12-S18, vol. 14.
Haffner S.M., "The Prediabetic Problem: Development of Non-Insulin-Dependent Diabetes Mellitus and Related Abnormalities.", *Journal of Diabetes and Its Complications*, Mar.-Apr. 1997, pp. 69-76, vol. 11(2).
Han et al., "Dapagliflozin, a Selective SGLT2 Inhibitor, Improves Glucose Homeostasis in Normal and Diabetic Rats.", *Diabetes*, Jun. 2008, pp. 1723-1729, vol. 57, New York.
Handlon, A. L., "Sodium glucose co-transporter 2 (SGLT2) inhibitors as potential antidiabetic agents.", *Expert Opin. Ther. Patents*, 2005, pp. 1531-1540, vol. 15(11).
Hixon et al., "Sizing Materials by Crushing and Grinding.", *Chemical Engineer*, Nov. 1990, pp. 94-103.
Hofslokken et al., "Convenient Method for the ortho-Formylation of Phenols.", *Acta Chemica Scandinavica*, 1999, pp. 258-262, vol. 53.
Hongu et al., "Na+-Glucose Cotransporter Inhibitors as Antidiabetic Agents. II.1) Synthesis and Structure—Activity Relationships of 4'-Dehydroxyphlorizin Derivatives.", *Chem. Pharm. Bull.*, 1998, pp. 22-33, vol. 46(1).
Horton et al., "Synthetic Routes to Higher-Carbon Sugars. Reaction of Lactones with 2-Lithio-1,3-Dithiane.", *Carbohydrate Research*, 1981, pp. 27-41, vol. 94.
Hu et al., "A New Approach Towards the Yellowing Inhibition of Mechanical Pulps. Part I: Selective Removal of alpha-Hydroxyl and alpha-Carbonyl Groups in Lignin Model Compounds.", *Holzforschung*, 1999, pp. 43-48, vol. 53(1).
Huang-Minlon, "Reduction of Steroid Ketones and other Carbonyl Compounds by Modified Wolff-Kishner Method.", *J. Am. Chem. Soc.*, Oct. 1949, pp. 3301-3303, vol. 71.
Ibrahim et al., "Facile Approach for the Selective Glycodisation of Cyclic Asymmetric Amides and Thioamides.", *Carbohydrate Letters*, 1996, pp. 425-432, vol. 1.
Ibrahim et al., "Selective Synthesis and Structure of 2-N- and 3-S-Glucosyl-1,2,4-Triazoles of Potential Biological Interest.", *Carbohydrate Letters*, 1999, pp. 331-338, vol. 3(5).
Idris et al., "Sodium-glucose co-transporter-2 inhibitors: an emerging new class of oral antidiabetic drug.", *Diabetes, Obesity and Metabolism*, 2009, pp. 79-88, vol. 11(2), GB, XP007915350.
Isaji, M., "Sodium-glucose cotransporter inhibitor for diabetes.", *Current Opinion in Investigational Drugs*, 2007, pp. 285-292, vol. 8(4).
Jain et al., "Polymorphism in Pharmacy.", *Indian Drugs*, 1986, pp. 315-329, vol. 23(6).
Kaelin et al., "General Strategies for the Synthesis of the Major Classes of C-aryl Glycosides.", *J. Am. Chem. Soc.*, 2001, pp. 6937-6938, vol. 123.
Kahn et al., "Normalization of Blood Glucose in Diabetic Rats with Phlorizin Treatment Reverses Insulin-resistant Glucose Transport in Adipose Cells without Restoring Glucose Transporter Gene Expression.", *Journal of Clinical Investigation*, 1991, pp. 561-570, vol. 87.
Kanai et al., "The Human Kidney Low Affinity Na+/Glucose Cotransporter SGLT2: Delineation of the Major Renal Reabsorptive Mechanism for D-Glucose.", *J. Clin. Invest.*, Jan. 1994, pp. 397-404, vol. 93.
Kasahara et al., "A missense mutation in the Na+/glucose cotransporter gene SGLT1 in a patient with congenital glucose-galactose malabsorption: normal trafficking but inactivation of the mutant protein.", *Biochimica et Biophysics Acta*, 2001, pp. 141-147, vol. 1536.
Katz et al., "Quantitative Insulin Sensitivity Check Index: A Simple, Accurate Method for Assessing Insulin Sensitivity in Humans.", *J. of Clin. Endrocrinology & Metabolism*, 2000, pp. 2040-2410, vol. 85(7).

(56) References Cited

OTHER PUBLICATIONS

Ketcha et al., "Synthesis of Alyl-Substituted N-Protected Indoles via Acylation and Reductive Deoxygenation1.", *J. Org. Chem.*, 1989, pp. 4350-4356, vol. 54.

Khan et al, "Reactions of Phenyl-Substituted Heterocyclic Compounds—II. Nitrations and Brominations of 1-Phenylpyrazole Derivatives.", *Canadian Journal of Chemistry*, 1963, pp. 1540-1547, vol. 41.

Kipnes, M., "Dapagliflozin: an emerging treatment option in type 2 diabetes.", *Expert Opinion Invest. Drugs*, 2009, pp. 327-334, vol. 18(3).

Kitagawa, K., et al., "Halogen-Magnesium Exchange via Trialkylmagnesates for the Preparation of Aryl- and Alkenylmagnesium Reagents.", *Angew. Chem. Int. Ed.*, 2000, pp. 2481-2493, vol. 39(14).

Klapars et al., "Copper-Catalyzed Halogen Exchange in Aryl Halides: An Aromatic Finkelstein Reaction.", *J. Am. Chem. Soc.*, 2002, pp. 14844-14845, vol. 124(50).

Knochel, P., et al., *Organic Reactions, vol. 58, Chapter 2: Preparation and Application of Functionalized Organozinc Compounds.*, 2001, pp. 417-490, Edited by L. E. Overman, et al., John Wiley &Sons, Inc., Publishers.

Komoroski et al., "Dapagliflozin, a Novel SGLT2 Inhibitor, Induces Dose-Dependent Glucosuria in Healthy Subjects.", Nature, May 2009, pp. 520-526, vol. 85(5).

Lee et al., "Recent Advances in Aryl C-Glycoside Synthesis.", *Current Topics in Medicinal Chemistry*, 2005, pp. 1333-1350, vol. 5.

Lee et al., "Synthesis and in Vitro Activity of Novel Isoxazolyl Tetrahydropyridinyl Oxazolidinone Antibacterial Agents.", *Bioorganic & Medicinal Chemistry Letters*, 2003, pp. 4117-4120, vol. 13.

Lieberman et al., "Pharmaceutical Dosage Forms.", Second Edition, 1990, Marcel Dekker Inc., pp. 462-472, vol. 2.

Lin et al., "Syntheses of Guanidinoglycosides with the Inventive use of Mitsunobu Conditions and 1, 8-Diazabicyclo[5.4.0]undec-7-ene.", *Synthesis*, 2003, pp. 255-261, No. 2.

Link et al., "A method for preparing C-glycosides related to phlorizin.", *Tetrahedron Letters*, 2000, pp. 9213-9217, vol. 41.

Lipscombe et al., "Trends in diabetes prevalence, incidence, and mortality in Ontario, Canada 1995-2005: a population-based study.", *Lancet*, 2007, vol. 369, pp. 750-756.

Maatooq et al., "C-p-Hydroxybenzoylglycoflavones From Citrullus Colocynthis.", *Phytochemistry*, Jan. 1997, pp. 187-190, vol. 44(1).

Mackenzie et al., "Biophysical Characteristics of the Pig Kidney Na+/Glucose Cotransporter SGLT2 Reveal a Common Mechanism for SGLT1 and SGLT2.", *J. Biol. Chem.*, 1996, vol. 271, pp. 32678-32683, No. 5.

Manis et al., "Metabolism of 4,4'-Methylenebis(2-chloroaniline) by Canine Liver and Kidney Slices.", *Drug Metabolism and Disposition*, 1986, pp. 166-174, vol. 14(2).

Marsenic, O. MD, "Glucose Control by the Kidney: An Emerging Target in Diabetes.", *Am. J. of Kidney Diseases*, May 2009, pp. 875-883, vol. 53(5).

Martin, S. F., "Unified Strategy for the Synthesis of C-aryl glycosides*.", *Pure Appl. Chem.*, 2003, pp. 63-70, vol. 75(1).

Matsuda et al., "Insulin Sensitivity Indices Obtained From Oral Glucose Tolerance Testing: Comparison with the euglycemic insulin clamp.", *Diabetes Care*, Sep. 1999, pp. 1462-1470, vol. 22(9).

Matthews et al., "Homeostasis model assessment: insulin resistance and—cell function from fasting plasma glucose and insulin concentrations in man.", *Diabetolgia*, 1985, pp. 412-419, vol. 28.

Meanwell et al., "Regiospecific Functionalization of 1,3-Dihydro-2H-benzimidazol-2-one and Structurally Related Cyclic Urea Derivates.", *J. Org. Chemistry*, 1995, pp. 1565-1582, vol. 60(6).

Meng et al., "Discovery of Dapagliflozin: a Potent, Selective Renal Sodium-Dependent Glucose Cotransporter 2 (SGLT2) Inhibitor for the Treatment of Type 2 Diabetes.", *J. Med. Chem.*, 2008, pp. 1145-1149, vol. 51(5).

Messaoudi et al, "Synthesis and biological evaluation of oxindoles and benzimidazolinones derivatives.", *European Journal of Medicinal Chemistry*, 2004,pp. 453-458, vol. 39.

Mewshaw et al., "New Generation Dopaminergic Agents. 7. Heterocyclic Bioisosteres that Exploit the 3-Oh-Phenoxyethylamine D2 Template.", *Bioorganic & Medicinal Chemistry Letters*, 1999, pp. 2593-2598, vol. 9.

Miyaura et al., "Palladium-Catalyzed Cross-Coupling Reactions of Organoboron Compounds.", *Chem. Rev.*, 1995, pp. 2457-2583, vol. 95(7).

Mongin, F., et al., "Deprotonation of furans using lithium magnesates.", *Tetrahedron Lett.*, 2005, pp. 7989-7992, vol. 46.

Nishimura et al, "Tissue-specific mRNA Expression Profiles of Human ATP-binding Cassette and Solute Carrier Transporter Superfamilies.", *Drug Metab. Pharmacokinet.*, 2005, pp. 452-477, vol. 20(6).

Nomura et al., "Discovery of canagliflozin, a novel C-glucoside with thiophene ring, as sodium dependent glucose cotransporter 2 inhibitor for the treatment of type 2 diabetes mellitus.", *Journal of Med. Chem.*, Sep. 9, 2012, pp. 6355-6360, vol. 53(17), American Chemical Society, US, XP007915324.

Nomura, S., "Renal Sodium-Dependent Glucose Cotransporter 2 (SGLT2) Inhibitors for New Anti-Diabetic Agent.", *Current Topics in Medicinal Chemistry*, 2010, pp. 411-418, vol. 10(4).

Ohsumi et al. "Pyrazole-O-Glucosides as Novel Na+-Glucose Cotransporter (SGLT) Inhibitors.", *Bioorganic & Medicinal Chemistry Letters*, 2003, pp. 2269-2272, vol. 13.

Oku et al., "T-1095, an Inhibitor of Renal Na+-Glucose Cotransporters, May Provide a Novel Approach to Treating Diabetes.", *Diabetes*, Sep. 1999, pp. 1794-1800, vol. 48.

Orjales et al. "New 2-Piperazinylbenzimidazole Derivatives as 5-HT-3 Antagonists. Synthesis and Pharmacological Evaluation.", *J. Med. Chem.*, 1997, pp. 586-593, vol. 40.

Parker et al., "Reductive Aromatization of Quinols: Synthesis of the C-Arylglycoside Nucleus of the Paulacandins and Chaetiacandin.", *Organic Letters*, 2000, pp. 497-499, vol. 2(4).

Parrott, E.L., "Milling of pharmaceutical solids.", *Journal of Pharmaceutical Sciences*, Jun. 1974, pp. 813-829, vol. 63(6).

Patani et al., "Bioisosterism: A Rational Approach in Drug Design.", *Chem. Rev., American Chemical Society*, 1996, pp. 3147-3176, vol. 96.

Peng et al., "Post-transcriptional Regulaton of Na+/Glucose Cotransporter (SGTL1) Gene Expression in LLC-PK1 Cells.", *Journal of Biological Chemistry*, 1995, pp. 20536-20542, vol. 270(35).

Perry's Chemical Engineers Handbook, Sixth Edition, 1984, pp. 21-13 to 21-19.

Pharmaceutical Sciences, Remington, 17th Ed., pp. 1585-1594 (1985).

Polshettiwar et al., "Pd-N-heterocycle carbene (NHR) organic silica: synthesis and application in carbon-carbon coupling reactions.", *Tetrahedron*, May 12, 2008, pp. 4637-4643, vol. 64(20), Elsevier Science Publishers, Amsterdam, NL, XP022607642.

Ramlo-Halsted B.A. & Edelman S.V., "The Natural History of Type 2 Diabetes Mellitus: Implications for Clinical Practice.", *Primary Care*, Dec. 1999, pp. 771-789, vol. 26(4).

Raynaud et al., "Revised Concept for the Estimation of Insulin Sensitivity From a Single Sample.", *Diabetes Care*, Jun. 1999, pp. 1003-1004, vol. 22(6).

Rosenstock et al., "Canagliflozin, an Inhibitor of Sodium Glucose Co-Transporter 2 (SGLT2), Improves Glycemic Control and Lowers Body Weight in Subjects with Type 2 Diabetes (T2D) on Metformin.", *Diabetes*, Jun. 1, 2010, pp. A21, vol. 59(supp. 1), American Diabetes Association, US, XP009139979.

Rosetti et al., "Correction of Hyperglycemia with Phlorizin Normalizes Tissue Sensitivity to Insulin in diabetic rats.", *Journal of Clinical Investigation*, 1987, pp. 1510-1515, vol. 79.

Rosetti et al., "Effect of Chronic Hyperglycemia on In Vivo Insulin Secretion in Partially Pancreatectomized Rats.", *Journal of Clinical Investigation*, 1987, pp. 1037-1044, vol. 80.

Rosetti et al., "Glucose Toxicity."; *Diabetes Care*, 1990, pp. 610-630, vol. 13.

(56) References Cited

OTHER PUBLICATIONS

Schmidt et al., "Synthese von Pyrazol-, Pyrazolo[3,4-d]pyrimidin- und 1H-1,2,4-Triazolgluconucleosiden aus Glucosehydrazonen.", *Liebigs Ann. Chem.*, 1981, pp. 2309-2317.
Translation—Schmidt et al., "Synthese von Pyrazol-, Pyrazolo[3,4-d]pyrimidin-und 1H-1,2,4-Triazolgluconucleosiden aus Glucosehydrazonen.", *Liebigs Ann. Chem.*, 1981, pp. 2309-2317.
Schultheiss et al., "Pharmaceutical Cocrystals and Their Physicochemical Properties.", *Crystal Growth and Design*, Jun. 3, 2009, pp. 2950-2967, vol. 9(6), XP55011939.
Shan et al., "The role of cocrystals in pharmaceutical science.", *Drug Discovery Today*, May 1, 2008, pp. 440-446, vol. 13(9-10), Elsevier, Rahway, NJ,US, XP022649919.
Silverman, R. B., "The Organic Chemistry of Drug Design and Drug Action.", Academic Press, 1992, pp. 19-23.
Somei et al., "The First and Simple Total Synthesis of Cappariloside $A^1$.", *Heterocycles*, 2000, pp. 1573-1578, vol. 53(7).
Srogl et al., "Sulfonium salts. Participants par excellence in metal-catalyzed carbon-carbon bond-forming reactions.", *Journal of the American Chemical Society*, Jan. 1, 1997, pp. 12376-12377, vol. 119, American Chemical Society, US, XP002955770.
Stoner et al., "Benzylation via Tandem Grignard Reaction—Lodotrimethylsilane (TMSI) Mediated.Reduction.", *Tetrahedron*, 1995, pp. 11043-11062, vol. 51(41).
Stumvoll et al., "Use of the Oral Glucose Tolerance Test to Assess Insulin Release and Insulin Sensitivity.", *Diabetes Care*, Mar. 2000, pp. 295-301, vol. 23(3).
Tanaka et al. "Solid-Phase Synthesis of—Mono-Substituted Ketones and an Application to the Synthesis of a Library of Phlorizin Derivatives.", *Synlett*, 2002, pp. 1427-1430, No. 9.
Thornber, C.T., "Isosterism and Molecular Modification in Drug Design.", *Chem. Society Review*, 1979, pp. 563-580, vol. 8.
Tilak et al, "Carcinogenesis by Thiophene Isosters of Polycyclic Hydrocarbons.", *Tetrahedron*, 1960, pp. 76-95, vol. 9.
Tsujihara et al., "Na+ Glucose Cotransporter (SGLT) Inhibitors as Antidiabetic Agents. 4. Synthesis and Pharmacological Properties of 4'-Dehydroxyphlorizin Derivatives Substituted on the B Ring.", *Journal of Medicinal Chemistry*, 1999, pp. 5311-5324, vol. 42.
Tsujihara et al., *Bio Clinica*, 1998, pp. 324-328, vol. 13(4), English language Abstract.
Turk et al., "Glucose/galactose malabsorption caused by a defect in the Na+/glucose cotransporter.", *Nature*, Mar. 1991, pp. 354-356, vol. 350.
Ueta et al., "Long-term treatment with the Na+-glucose contransporter inhibitor T1095 causes sustained improvement in hyperglycemia and prevents diabetic neuropathy in Goto-Kakizaki Rats.", *Life Sci.*, 2005, pp. 2655-2668, vol. 76(23).
Unger et al., "Hyperglycemia as an inducer as well as a consequence of impaired islet cell function and insulin resistance: implications for the management of diabetes.", *Diabetologia*, 1985, pp. 119-121, vol. 28.
Vippagunta et al., "Crystalline Solids.", *Advanced Drug Delivery Reviews*, 2001, pp. 3-26, vol. 48.
Vishweshwar et al., "Pharmaceutical co-crystals.", *Journal of Pharmaceutical Sciences*, Mar. 1, 2006, pp. 499-516, vol. 95(3), American Pharmaceutical Association, Washington, US.
Wallace et al., "Use and Abuse of Homa Modeling.", *Diabetes Care*, Jun. 2004, pp. 1487-1495, vol. 27(6).
Wang et al, "Selective monolithiation of 2,5-dibromopyridine with butyllithium.", *Tetrahedron Letters*, 2000, pp. 4335-4338, vol. 41.
Wareham et al., "Is There Really an epidemic of diabetes?", *Diabetologia*, 2005, pp. 1454-1455, vol. 48.
Washburn, W. N., "Evolution of sodium glucose co-transporter 2 inhibitors as anti-diabetic agents.", *Expert Opin. Ther. Patents*, 2009, pp. 1485-1499, vol. 19(11).
Watanabe et al., "Cyclopentyl Methyl Ether as a New and Alternative Process Solvent.", *Organic Process Research and Development*, 2007, pp. 251-258, vol. 11.

Wild et al., "Global Prevalence of Diabetes: Estimates for the year 2000 and projections for 2030.", *Diabetes Care*, May 2004, pp. 1047-1053, vol. 27(5).
Wolff, M. E., vol. 1: *Principles and Practice, Burger's Medicinal Chemistry and Drug Discovery*, 5th Edition, 1995, pp. 975-977.
Wright, E.M., "Renal Na+-glucose cotransporters.", *Am J Physiol Renal Physiol*, 2001, pp. F10-F18, vol. 280.
Wurster D.E., "Air-suspension Technique of Coating Drug Particles* a Preliminary Report.", *Journal of the American Pharmaceutical Association*, Aug. 1959, pp. 451-454, vol. 48(8).
Wurster, D.E., "Preparation of compressed tablet granulations by the air-suspension technique II.", *Journal of the American Pharmaceutical Association*, 1960, pp. 82-84, vol. 49(2).
Yang et al., "Convergent C-Glycolipid Synthesis via the Ramberg-Backlund Reaction: Active Antiproliferative Glycolipids.", *Org. Lett.* 1999, pp. 2149-2151, vol. 1913).
Yoshimura et al., "Discovery of Novel and PotenCRetinoic Acid Receptor alpha—Agonists: Synthesis and Evaluation of Benzofuranyl-pyrrole and Benzothiophenyl-pyrrole Derivatives," *J. Med. Chem.*, 2000, pp. 2929-2937, vol. 43.
Zamani et al., "Synthesis and Structure Determination of Some New N-Glycosides of 4,5-Disubstituted-1,2,4-triazole-3-thiones.", *Journal of the Chinese Chemical Society*, 2002, pp. 1041-1044, vol. 49.
Zhdanov, Y. et al., "Application of organozinc compounds in the synthesis of carbon-carbon derivatives of sugars.", 2001, Database CA (online), Chemical Abstracts Service, Columbus, Ohio, USA, XP002612365.
Translation—Zhdanov, Y. et al., "Application of organozinc compounds in the synthesis of carbon-carbon derivatives of sugars.", 2001, Database CA (online), Chemical Abstracts Service, Columbus, Ohio, USA, XP002612365.
Zhou, F. Y., "The Synthesis and Characterization of 1-Benzyl-3-N-(Beta-D-glucosie-1-yl)-4-fluorouracil.", *Hecheng Huaxue*, 2001, pp. 272-274, vol. 9(3).
Jianqun, et al., "Recent advances in palladium catalysts for aryl chlorides coupling reaction", *Industrial Catalysis*, Jul. 31, 2005, pp. 29-44, vol. 13(7).
Zhiyin, et al., "Cross-coupling reaction of Grignard reagent with thiophenyl halides by using nickel phosphine as catalyst and the synthesis of αterthienyl", *Huaxue Shiji*, Dec. 31, 1995, pp. 289-290, vol. 17(5).
Byrn et al., "Pharmaceutical Solids: A Strategic Approach to Regulatory Considerations.", *Pharml. Res.*, 1995, pp. 945-954, vol. 12(7).
Bavin, M., "Process Development: Polymorphism in Process Development.", *Chemistry & Industry*, 1989, pp. 527-529, vol. 16.
Kozikowski et al., "Organometallics in Organic Synthesis. Applications of a New Diorganozinc Reaction to the Synthesis of C-Glycosyl Compounds With Evidence for an Oxonium-Ion Mechanism*.", *Carbohydrate Research*, 1987, pp. 109-124, vol. 171.
Asahara et al. *Handbook of Solvents*, K.K. Kodansah., Sep. 1, 1985, Sixth Printing, pp. 47-51, Tokyo, JP.
Clinical Trial NTC00642278, Clinical Trials.gov/archive/NTC00642278, View of Trial on Jun. 20, 2009.
Clinical Trial, "An Efficacy, Safety, and Tolerability Study of Canagliflozin (JNJ-28431754) in Patients With Type 2 Diabetes.", Clinical Trial NTC00642278, accessed Mar. 20, 2015.
International Search Report relating to International Application No. PCT/US2010/041136, Date of Mailing of International Search Report, dated Oct. 27, 2010.
Written Opinion, relating to International Application No. PCT/US2010/041136, Date of Mailing of Written Opinion, dated Oct. 27, 2010.
832133-18-0, Registry File, Mar. 4, 2005.
*A Textbook of Hospital and Clinical Pharmacology*, 28th edition, Paradkar, A.R. and Chunawala, S.A., Chapter 25, Bioavailability of Drugs, 1991, pp. 25.1, 25.3 and 25.4.
Brandsma et al., "Nickel- and Palladium-Catalyzed Cross-Coupling Reactions With Organometallic Intermediates.", *Application of Transition Metal Catalysts in Organic Synthesis*, 1999, Chapter 11, pp. 227-230, 243-246, 250-252, 258, 261, 273, Springer-Verlag Berlin Heidelberg, Germany.

(56) References Cited

OTHER PUBLICATIONS

*Encyclopedia of Pharmaceutical Technology*, Editors James Swarbrick and James C. Boylan; vol. 4, Design of Drugs to Drying and Driers, 1991 cover pages and pp. 209-229.
*Encyclopedia of Pharmaceutical Technology*, Science Press, J. Swarbrick et al. editors, 2008, vol. 3, pp. 1821-1828 (A Chinese Textbook).
FMC Health and Nutrition, "Tablet Ingredients", Section 4, Dr. Zak Chowhan; published: 1998, pp. 1-18.
Kravovskiy et al., "A LiCl-Mediated Br/Mg—exchange reaction for produce functionalized aryl- and heteroarylmagnesium connections starting from organic bromides.", *Angew. Chem.*, 2004, pp. 3396-3399, vol. 116.
Kravovskiy et al., "Highly efficient reagents for the bromine-magnesium exchange.", *Angew. Chem.*, 2006, pp. 165-169, vol. 118.
*Pharmacy*, 6th edition, People's Publishing House, Cui Fude editor, 2008, pp. 125-135.
Remington, "*The Science and Practice of Pharmacy*", 21st Edition, Lippincott Williams & Wilkins, Editor: David B. Troy, Chapter 35; 2006, Cover pages and pp. 677-678.
Remington, "The Science and Practice of Pharmacy", 21st Edition, Lippincott Williams & Wilkins, Editor: David Troy, Chapter 45; 2006, Cover pages and pp. 891-892.
Ritschel et al., "Die Tablette", *Handbuch der Entwicklung, Herstellung und Qualitatssicherung, 2. Vollstandig Oberarbeitete und erweiterte Auflage*, Editio Cantor Verlag Aulendorf, 2002, pp. 64-65.
Schernthaner et al., "Erratum", *Diabetes Care*, Dec. 2013, p. 4172, vol. 36.
Takada, N., "Screening and selection of active pharmaceutical ingredient forms at the stage of drug development.", *Pharm Stage*, Jan. 15, 2007, vol. 6, No. 10, pp. 20-25.
*The Extra Pharmaceutical Necessitits*, Sichuan Publishing House of Science & Technology, Luo Mingsheng edit, 1993, vol. 3, pp. 73-79.
Tobyn et al., "Physicochemical comparison between microcrystalline cellulose and silicified microcrystalline cellulose.", *International Journal of Pharmaceutics*, Jul. 15, 1998, pp. 183-194, vol. 169(2).
Veen et al., "Compaction Mechanism and tablet strength of unlubricated and lubricated (silicified) microcrystalline cellulose.", *European Journal of Pharmaceutics and Biopharmaceuticals*, 2005, pp. 133-138, vol. 59.
Wang, Wen-Ling et al., *Chinese Journal of Clinical Pharmacology*, 1992, vol. 8(1). pp. 25-31.
Yamada, M., *Strategy and Novel Technology on Pharmaceutical Preparations*, CMC Publishing Co., Ltd., Mar. 31, 2007, First Copy, p. 152-171.
Yuan et al., "Pharmaceuticals Cocrystals.", *Progress in Chemistry*, May 2010, pp. 829-836, vol. 22(5).
Musso, et al., "A novel Approach to control hyperglycemia in type 2 diabetes; sodium glucose co-transport (SGLT) inhibitors; systematic review and meta-analysis of randomized trials.", *Annals of Medicine*, Jun. 2012, pp. 375-393, vol. 44(4), XP0055098643.
Veen et al., "Compaction mechanism and tablet strength of unlubricated and lubricated (silicified) microcrystalline cellulose.", *EP J. Phar. and Biopharm.*, 2005, pp. 133-138, vol. 59.
EPO Communication Of Notices Of Opposition, dated Feb. 18, 2020.
Opposition 01—Teva Pharmaceutical Industries Ltd., Jan. 31, 2020.
Opposition 02—Generics [UK] Limited, Jan. 31, 2020.
EMEA Summary of Opinion, Vokanamet®, canagliflozin/metformin, Feb. 20, 2014.
Schernthaner et al., "Canagliflozin Compared with Sitagliptin for Patients With Type 2 Diabetes Who Do Not Have Adequate Glycemic Control With Metformin Plus Sulfonylurea.", Diabetes Care, Sep. 2013, pp. 2508-2515, vol. 36.
EMEA Assessment Report, Vokanamet®, canagliflozin/metformin, Feb. 20, 2014.
Rosenstock et al., "Initial Combination Therapy With Canagliflozin Plus Metformin Versus Each Component as Monotherapy for Drug Naïve Type 2 Diabetes.", Diabetes Care, Mar. 2016, pp. 353-362, vol. 39.
Abstract 77-OR, "Canagliflozin, an inhibitor of Sodium Glucose Co-Transporter 2 (SGLT2), Improves Glycemic Control and Lowers Body Weight in Subjects with Type 2 Diabetes (T2D) on Metformin.", Proceedings of the 130th Meeting of the Pharmaceutical Society of Japan, Mar. 28-30, 2010.
International Nonproprietary Names for Pharmaceutical Substances (INN), World Health Organization, Canagliflozin, 2009, pp. 319-324, vol. 23(4).
Abstract S38-1, "Discovery of Canagliflozin as SGLT2 inhibitor for the Treatment of Type 2 Diabetes Mellitus.", Proceedings of the 130th Meeting of the Pharmaceutical Society of Japan, Mar. 28-30, 2010.
WHO Model List of Essential Medicines, 16th edition, Mar. 2009, pp. 1-39.
Lachman et al., The Theory and Practice of Industrial Pharmacy, Third Edition, 1987, pp. 233-234.
Center For Drug Evaluation, Application No. 21-178, Approval Letter, Jul. 31, 2000.
Davidson et al., "Tolerability Profile of Metformin/Glibenclamide Combination Tablets (Glucovance®). A New Treatment for the Management of Type 2 Diabetes Mellitus.", Drug Safety, 2004, pp. 1205-1216, vol. 27(15).
Komorski et al., "Dapagliflozin (BMS-512148), a selective inhibitor of the sodium glucose uptake transporter 2 (SGLT2), reduces fasting serum glucose and glucose excursion in type 2 diabetes mellitus patents over 14 days.", Diabetes, 2007, pp. A49.
Email from the American Diabetes Association relating to publication of Komorski.
Pharmaceutical Dosage Forms, Tablets, vol. 1, Edited by Herbert A. Liberman, Leon Lachman and Joseph B. Schwartz, Marcel Dekker, Inc., 1989, pp. 105-106, 152, 173-174.
"Cellulose, Microcrystalline.", Handbook of Pharmaceutical Excipients, Third Edition, Edited by Arthur H. Kibbe, 2000, pp. 102-106.
Bayer Case T007/07, Boards of Appeal of European Patent Office, Datasheet for Decision of Jul. 7, 2011.
"Starch.", Handbook of Pharmaceutical Excipients, Second Edition, Edited by Ainley Wade and Paul J. Weller, 1994, pp. 483-487.
Remington: The Science and Practice of Pharmacy., Edited by Alfonso R. Genaro, 20th Edition, 2000, pp. 861, 1047-1048.
Patentee's Response To the Oppositions, Corresponding European Patent 2451482B1; Patentee: Janssen Pharmaceutica NV.
D34: Bailey, C.J., "Hypoglycaemic and anti-hyperglycaemic drugs for the control of diabetes.", Proceedings of The Nutrition Society, 1991, pp. 619-630, vol. 50.
D35: Declaration of Norman Rosenthal included in Patentee's Response To the Oppositions, Corresponding European Patent 2451482B1; Patentee: Janssen Pharmaceutica NV.
Ashiya, M. and Smith, R., "Non-insulin therapies for type-2 diabetes.", Nature Reviews, Drug Discovery, Oct. 6, 2007, pp. 777-778, vol. 6.
De Valk, H.W., "DPP-4 Inhibitors and Combined Treatment in Type 2 Diabetes: Re-evaluation of Clinical Success and Safety.", The Review of Diabetic Studies, Apr. 2007, pp. 126-133.
Turner et al., "Glycemic Control With Diet, Sulfoonylurea, Metformin, or Insulin in Patients With Type 2 Diabetes Mellitus. Progressive Requirement for Multiple Therapies (UKPDS 49).", JAMA, Jun. 2, 1999, pp. 2005-2012, vol. 281(21).
Zimmerman et al., "Multi-target therapeutics: when the whole is greater than the sum of the parts.", Drug Discovery Today, Jan. 2007, pp. 34-42, vol. 12(1/2).
Summons To Attend Oral Proceedings Pursuant to Rule 115(1) EPC and Preliminary Opinion, Issued by EPC on Dec. 10, 2020 in related granted EP Patent No. 2451482 (App. No. 10735109.0).
D9a, Idris et al.(D9), showing on-line publication date of Dec. 29, 2008.
Glucophage, Glucophage XR Label, Bristol-Myers Squibb Company, NDA 20-357/S-031 and NDA 21-202/S-016, Aug. 27, 2008.
Wikipedia pages for biguanides, phenformin, buformin; Apr. 14, 2021.

(56) References Cited

OTHER PUBLICATIONS

Bedekar et al., "Natural Products for Type II Diabetes Treatment.", Advances in Applied Microbiology, vol. 71, Chapter 2, pp. 60-63, Feb. 2010.
FPA Highlights of prescribing info for Xigduo XR.
Pharmaceutical Posage Forms, Tablets, vol. 1, Edited by Herbert A. Liberman, Leon Lachman and Joseph B. Schwartz, Marcel Pekker, Inc., 1989, pp. 110-116.
Response to Communication from Opposition Division of Dec. 10, 2020, Opposition against EP2451482, Teva Pharmaceutical Industries Ltd., Apr. 21, 2021.
Generics [UK] Limited, Further Submissions, Reply to the patentee's response to the notices of opposition, Apr. 21, 2021.
Decision of Oral Proceedings in corresponding EP patent No. 2451482 (EP application No. 10735109.0), dated Sep. 24, 2021.
Proprietor submission in advance of Oral Proceedings, Jun. 11, 2021.
Decision Revoking the European Patent EP-B-2 451 482, dated Nov. 9, 2021.
Minutes of Oral Proceeding, dated Nov. 9, 2021.
Komorski et al., "Dapagliflozin, a Novel, Selective SGLT2 Inhibitor, Improved Glycemic Control Over 2 Weeks in Patients With Type 2 Diabetes Mellitus.", Clinical Pharmacology & Therapeutics, May 2009, pp. 513-519, vol. 85(5).
Appellant Statement of Grounds of Appeal; EP Patent 2451482B1.
Press Release—First Phase II Short-Term Study on Dapagliflozin Shows Results on Safety Tolerability and Glycemic Markers in Subjects with Type 2 Diabetes. 2007.
Opponent Reply to Notice of Appeal, dated Aug. 15, 2022, Generics [UK] Ltd.
Opponent Reply to Notice of Appeal, dated Aug. 17, 2022, TEVA.

\* cited by examiner

COMBINATION THERAPY FOR THE TREATMENT OF DIABETES

CROSS REFERENCE TO RELATED APPLICATIONS

This application is a continuation of U.S. patent application Ser. No. 14/964,670, filed Dec. 10, 2015, which is a continuation of U.S. patent application Ser. No. 14/452,884, filed Aug. 6, 2014, abandoned, which is a continuation of U.S. patent application Ser. No. 12/830,479, filed on Jul. 6, 2010, abandoned, which claims the benefit of U.S. Provisional Application 61/223,881, filed on Jul. 8, 2009, the disclosures of which are hereby incorporated by reference herein in their entireties.

FIELD OF THE INVENTION

The present invention is directed to co-therapy and methods for the treatment and prevention of glucose-related disorders such as Type 2 diabetes mellitus and Syndrome X. The present invention is further directed to pharmaceutical compositions for the co-therapy and methods described herein.

BACKGROUND OF THE INVENTION

Diabetes mellitus is a medical term for the presence of elevated blood glucose. People with diabetes either don't produce insulin, produce too little insulin or do not respond to insulin, resulting in the build up of glucose in the blood. The most common form of diabetes is Type 2 diabetes, once referred to as adult onset diabetes or non-insulin dependent diabetes (NIDDM), which may account for >90% of diabetes in adults. However, as the younger population becomes increasingly overweight or obese, Type 2 diabetes is becoming more prevalent in teens and children. Diabetes may also refer to gestational diabetes, Type 1 diabetes or autoimmune diabetes, once referred to as juvenile onset diabetes and type 1½ diabetes, also referred to as latent-autoimmune diabetes in adults or LADA. Diabetes may occur because of poor dietary habits or lack of physical activity (e.g., sedentary lifestyle), genetic mutations, injury to the pancreas, drug (e.g., AIDS therapies) or chemical (e.g., steroid) exposure or disease (e.g., cystic fibrosis, Down syndrome, Cushing's syndrome). Two rare types of genetic defects leading to diabetes are termed maturity-onset diabetes of the young (MODY) and atypical diabetes mellitus (ADM).

Type 2 diabetes mellitus (non-insulin-dependent diabetes mellitus or NIDDM) is a metabolic disorder involving disregulation of glucose metabolism and insulin resistance, and long-term complications involving the eyes, kidneys, nerves, and blood vessels. Type 2 diabetes mellitus usually develops in adulthood (middle life or later) and is described as the body's inability to make either sufficient insulin (abnormal insulin secretion) or its inability to effectively use insulin (resistance to insulin action in target organs and tissues). More particularly, patients suffering from Type 2 diabetes mellitus have a relative insulin deficiency. That is, in these patients, plasma insulin levels are normal to high in absolute terms, although they are lower than predicted for the level of plasma glucose that is present.

Type 2 diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Syndrome X, also termed Insulin Resistance Syndrome (IRS), Metabolic Syndrome, or Metabolic Syndrome X, is a disorder that presents risk factors for the development of Type 2 diabetes mellitus and cardiovascular disease including glucose intolerance, hyperinsulinemia and insulin resistance, hypertriglyceridemia, hypertension and obesity.

The diagnosis of Type 2 diabetes mellitus includes assessment of symptoms and measurement of glucose in the urine and blood. Blood glucose level determination is necessary for an accurate diagnosis. More specifically, fasting blood glucose level determination is a standard approach used. However, the oral glucose tolerance test (OGTT) is considered to be more sensitive than fasted blood glucose level. Type 2 diabetes mellitus is associated with impaired oral glucose tolerance (OGT). The OGTT thus can aid in the diagnosis of Type 2 diabetes mellitus, although generally not necessary for the diagnosis of diabetes (Emancipator K, Am J Clin Pathol 1999 November; 112(5):665-74; Type 2 Diabetes Mellitus, Decision Resources Inc., March 2000). The OGTT allows for an estimation of pancreatic beta-cell secretory function and insulin sensitivity, which helps in the diagnosis of Type 2 diabetes mellitus and evaluation of the severity or progression of the disease (e.g., Caumo A, Bergman R N, Cobelli C, J Clin Endocrinol Metab 2000, 85(11): 4396-402). More particularly, the OGTT is extremely helpful in establishing the degree of hyperglycemia in patients with multiple borderline fasting blood glucose levels that have not been diagnosed as diabetics. In addition, the OGTT is useful in testing patients with symptoms of Type 2 diabetes mellitus where the possible diagnosis of abnormal carbohydrate metabolism has to be clearly established or refuted.

Thus, impaired glucose tolerance is diagnosed in individuals that have fasting blood glucose levels less than those required for a diagnosis of Type 2 diabetes mellitus, but have a plasma glucose response during the OGTT between normal and diabetics. Impaired glucose tolerance is considered a pre-diabetic condition, and impaired glucose tolerance (as defined by the OGTT) is a strong predictor for the development of Type 2 diabetes mellitus (Haffner S M, Diabet Med 1997 August; 14 Suppl 3:S12-8).

Type 2 diabetes mellitus is a progressive disease associated with the reduction of pancreatic function and/or other insulin-related processes, aggravated by increased plasma glucose levels. Thus, Type 2 diabetes mellitus usually has a prolonged pre-diabetic phase and various pathophysiological mechanisms can lead to pathological hyperglycemia and impaired glucose tolerance, for instance, abnormalities in glucose utilization and effectiveness, insulin action and/or insulin production in the prediabetic state (Goldberg R B, Med Clin North Am 1998 July; 82(4):805-21).

The pre-diabetic state associated with glucose intolerance can also be associated with a predisposition to abdominal obesity, insulin resistance, hyperlipidemia, and high blood pressure, that is, Syndrome X (Groop L, Forsblom C, Lehtovirta M, Am J Hypertens 1997 September; 10(9 Pt 2):172S-180S; Haffner S M, J Diabetes Complications 1997 March-April; 11(2):69-76; Beck-Nielsen H, Henriksen J E, Alford F, Hother-Nielson O, Diabet Med 1996 September; 13(9 Suppl 6):578-84).

Thus, defective carbohydrate metabolism is pivotal to the pathogenesis of Type 2 diabetes mellitus and impaired glucose tolerance (Dinneen S F, Diabet Med 1997 August; 14 Suppl 3:S19-24). In fact, a continuum from impaired glucose tolerance and impaired fasting glucose to definitive Type 2 diabetes mellitus exists (Ramlo-Halsted B A, Edelman S V, Prim Care 1999 December; 26(4):771-89).

Early intervention in individuals at risk to develop Type 2 diabetes mellitus, focusing on reducing the pathological hyperglycemia or impaired glucose tolerance may prevent or delay the progression towards Type 2 diabetes mellitus and associated complications and/or Syndrome X. Therefore, by effectively treating impaired oral glucose tolerance and/or elevated blood glucose levels, one can prevent or inhibit the progression of the disorder to Type 2 diabetes mellitus or Syndrome X.

Typical treatment of glucose disorders including Type 2 diabetes mellitus and Syndrome X focuses on maintaining the blood glucose level as near to normal as possible and includes diet and exercise, and when necessary, treatment with anti-diabetic agents, insulin or a combination thereof. Type 2 diabetes mellitus that cannot be controlled by dietary management is treated with oral antidiabetic agents including, but not limited to, sulfonylureas (e.g., not limited to first generation: chlorpropamide, tolazamide, tolbutamide; second generation: glyburide, glipizide; and third generation: glimepiride), biguanides (e.g., metformin), thiazolidinediones (e.g., rosiglitazone, pioglitazone, troglitazone), alpha-glucosidase inhibitors (e.g., acarbose, miglitol), meglitinides (e.g., repaglinide), other insulin-sensitizing compounds, and/or other anti-obesity agents (e.g., orlistat or sibutramine). For Syndrome X, the anti-diabetic agents are additionally combined with pharmacological agents for the treatment of the concomitant co-morbidities (e.g., antihypertensives for hypertension, hypolipidemic agents for hyperlipidemia).

First-line therapies typically include metformin and sulfonylureas as well as thiazolidinediones. Metformin monotherapy is a first line choice, particularly for treating Type 2 diabetic patients who are also obese and/or dyslipidemic. Lack of an appropriate response to metformin is often followed by treatment with metformin in combination with sulfonylureas, thiazolidinediones, or insulin. Sulfonylurea monotherapy (including all generations of drugs) is also a common first line option. Another first line therapy choice may be thiazolidinediones. Patients who do not respond appropriately to oral anti-diabetic monotherapy, are given combinations of these agents. When glycemic control cannot be maintained with oral antidiabetics alone, insulin therapy is used either as a monotherapy, or in combination with oral antidiabetic agents. These same strategies, optionally in combination with additional strategies (e.g., antihypertensive) can be used for the treatment of Syndrome X.

Anti-diabetic agents include, but are not limited to:

(a) Sulfonylureas, which increase insulin production by stimulating pancreatic beta cells, and therefore act as insulin secretagogues. The primary mechanism of action of sulfonylureas is to close ATP-sensitive potassium channels in the beta-cell plasma membrane, initiating a chain of events that result in insulin release. Suitable examples of sulfonylureas include, but are not limited to chlorpropamide, tolazamide, tolbutamide, glyburide, glipizide, glimepiride, and like.

(b) Meglitinides, another class of insulin secretagogues, that have a mechanism of action distinct from that of the sulfonylureas. Suitable examples of meglitinides include, but are not limited to repaglinide.

(c) Agents which modify insulin secretion such as Glucagon-like Peptide-1 (GLP-1) and it's mimetics, Glucose-insulinotropic peptide (GIP) and it's mimetics, Exendin and it's mimetics, and Dipeptyl Protease Inhibitors (DPPIV).

(d) Biguanides which decrease liver glucose production and increase the uptake of glucose. Suitable examples include, but are not limited to metformin.

(e) Thiazolidinediones, insulin sensitizing drugs which decrease peripheral insulin resistance by enhancing the effects of insulin at target organs and tissues. These drugs bind and activate the nuclear receptor, peroxisome proliferator-activated receptor-gamma (PPAR-gamma) which increases transcription of specific insulin-responsive genes. Suitable examples of PPAR-gamma agonists are the thiazolidinediones which include, but are not limited to rosiglitazone, pioglitazone, troglitazone, isaglitazone (known as MCC-555), 2-[2-[(2R)-4-hexyl-3,4-dihydro-3-oxo-2H-1,4-benzoxazin-2-yl]ethoxy]-benzene acetic acid, and the like. Additionally, the non-thiazolidinediones also act as insulin sensitizing drugs, and include, but are not limited to GW2570, and the like.

(f) Retinoid-X receptor (RXR) modulators, also insulin sensitizing drugs, which include, but are not limited to targretin, 9-cis-retinoic acid, and the like.

(g) Other insulin sensitizing agents include, but are not limited to INS-1, PTP-1B inhibitors, GSK3 inhibitors, glycogen phosphorylase a inhibitors, fructose-1,6-bisphosphatase inhibitors, and the like.

(h) Alpha-glucosidase inhibitors which act to inhibit alpha-glucosidase. Alpha-glucosidase converts fructose to glucose, thus these inhibitors delay the digestion of carbohydrates. The undigested carbohydrates are subsequently broken down in the gut, thereby reducing the post-prandial glucose peak. Suitable examples include, but are not limited to, acarbose and miglitol.

(i) Insulins, including regular or short-acting, intermediate-acting, and long-acting insulins, inhaled insulin and insulin analogues such as insulin molecules with minor differences in the natural amino acid sequence. These modified insulins may have faster onset of action and/or shorter duration of action.

(j) Small molecule mimics of insulin, including, but not limited to L-783281, TE-17411, and the like.

(k) Na-glucose co-transporter inhibitors which inhibit the renal reabsorption of glucose such as T-1095, T-1095A, phlorizin, and the like.

(l) Amylin agonists which include, but are not limited to pramlintide, and the like.

(k) Glucagon antagonists such as AY-279955, and the like.

In addition to antidiabetic agents, therapies may include add-on treatment with anti-obesity agents such as orlistat, a pancreatic lipase inhibitor, which prevents the breakdown and absorption of fat; or sibutramine, an appetite suppressant and inhibitor of the reuptake of serotonin, norepinephrine and dopamine in the brain. Other potential add-on anti-obesity agents include, but are not limited to, appetite-suppressants acting through adrenergic mechanisms such as benzphetamine, phenmetrazine, phentermine, diethylpropion, mazindol, sibutramine, phenylpropanolamine or, ephedrine; appetite-suppressant agents acting through serotonergic mechanisms such as quipazine, fluoxetine, sertraline, fenfluramine, or dexfenfluramine; appetite-suppressant agents acting through dopamine mechanisms, eg, apomorphine; appetite-suppressant agents acting through histaminergic mechanisms (eg, histamine mimetics, H3 receptor modulators); enhancers of energy expenditure such as beta-3 adrenergic agonists and stimulators of uncoupling protein function; leptin and leptin mimetics; neuropeptide Y antagonists; melanocortin-1, 3 and 4 receptor modulators; cholecystokinin agonists; glucagon-like peptide-1 (GLP-1) mimetics and analogues (eg, Exendin); androgens (eg, dehydroepiandrosterone and derivatives such as etiocholandione), testosterone, anabolic steroids (eg, oxandrolone), and steroidal hormones; galanin receptor antagonists; cytokine agents such as ciliary neurotrophic factor; amylase inhibitors; enterostatin agonists/mimetics; orexin/hypocretin antagonists; urocortin antagonists; bombesin agonists; modulators of protein kinase A; corticotropin-releasing factor mimetics; cocaine- and amphetamine-regulated transcript mimetics; calcitonin-gene related peptide mimetics; and fatty acid synthase inhibitors.

There remains a need to provide an effective treatment for glucose related disorders such as elevated glucose levels, Type 2 diabetes mellitus, Syndrome X, and the like. There also remains a need to provide an effective treatment for glucose related disorders which also slows or prevents the progression and/or development of Type 2 diabetes mellitus.

SUMMARY OF THE INVENTION

The present invention is directed to methods of co-therapy for the treatment and prevention of glucose-related disorders, said methods comprising administering to a subject in need thereof a therapeutically effective amount of co-therapy comprising (a) metformin or a pharmaceutically acceptable salt thereof and (b) a compound of formula (I)

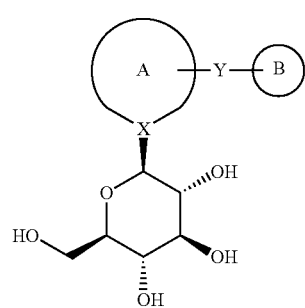

(I)

wherein Ring A and Ring B are one of the followings:

(1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring; or (2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring; or (3) Ring A is an optionally substituted unsaturated fused heterobicyclic ring, wherein the sugar moiety X-(sugar) and the moiety —Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;

X is a carbon atom or a nitrogen atom; and

Y is —(CH$_2$)$_n$— (wherein n is 1 or 2);

or a pharmaceutically acceptable salt thereof, or a prodrug thereof.

The present invention is further directed to methods of co-therapy for the treatment and prevention of glucose-related disorders, said methods comprising administering to a subject in need thereof a therapeutically effective amount of co-therapy comprising (a) glyburide and (b) a compound of formula (I) or pharmaceutically acceptable salt thereof.

The present invention is further directed to (a) a compound of formula (I) or pharmaceutically acceptable salt thereof in combination with (b) metformin or a pharmaceutically acceptable salt thereof for use in the treatment and prevention of glucose-related disorders The present invention is further directed to (a) a compound of formula (I) or pharmaceutically acceptable salt thereof in combination with (b) metformin or a pharmaceutically acceptable salt thereof and (c) a sulfonylurea (preferably glyburide) or pharmaceutically acceptable salt thereof for use in the treatment and prevention of glucose-related disorders.

The present invention is further directed to methods of co-therapy for the treatment and prevention of glucose-related disorders, said methods comprising administering to a subject in need thereof a therapeutically effective amount of co-therapy comprising (a) metformin or a pharmaceutically acceptable salt thereof and (b) a compound of formula (I) or pharmaceutically acceptable salt thereof and (c) a sulfonylurea (preferably glyburide) or pharmaceutically acceptable salt thereof.

The present invention is further directed to a pharmaceutical composition comprising (a) metformin or a pharmaceutically acceptable salt thereof, (b) a compound of formula (I) or pharmaceutically acceptable salt thereof and (c) a pharmaceutically acceptable excipient. An illustration of the invention is a pharmaceutical composition made by mixing comprising (a) metformin or a pharmaceutically acceptable salt thereof, (b) a compound of formula (I) or pharmaceutically acceptable salt thereof and (c) a pharmaceutically acceptable excipient. Illustrating the invention is a process for making a pharmaceutical composition comprising mixing comprising (a) metformin or a pharmaceutically acceptable salt thereof, (b) a compound of formula (I) or pharmaceutically acceptable salt thereof and (c) a pharmaceutically acceptable excipient.

The present invention is further directed to a pharmaceutical composition comprising (a) a sulfonylurea (preferably glyburide) or a pharmaceutically acceptable salt thereof, (b) a compound of formula (I) or pharmaceutically acceptable salt thereof and (c) a pharmaceutically acceptable excipient. An illustration of the invention is a pharmaceutical composition made by mixing comprising (a) a sulfonylurea (preferably glyburide) or a pharmaceutically acceptable salt thereof, (b) a compound of formula (I) or pharmaceutically acceptable salt thereof and (c) a pharmaceutically acceptable excipient. Illustrating the invention is a process for making a pharmaceutical composition comprising mixing comprising (a) a sulfonylurea (preferably glyburide) or a pharmaceutically acceptable salt thereof, (b) a compound of formula (I) or pharmaceutically acceptable salt thereof and (c) a pharmaceutically acceptable excipient.

The present invention is further directed to a pharmaceutical composition comprising (a) metformin or a pharmaceutically acceptable salt thereof, (b) a compound of formula (I) or pharmaceutically acceptable salt thereof, (c) a sulfonylurea or pharmaceutically acceptable salt thereof, and (d) a pharmaceutically acceptable excipient. An illustration of the invention is a pharmaceutical composition made by mixing comprising (a) metformin or a pharmaceutically acceptable salt thereof, (b) a compound of formula (I) or pharmaceutically acceptable salt thereof, (c) a sulfonylurea or pharmaceutically acceptable salt thereof, and (d) a pharmaceutically acceptable excipient. Illustrating the invention is a process for making a pharmaceutical composition comprising mixing comprising (a) metformin or a pharmaceutically acceptable salt thereof, (b) a compound of formula (I) or pharmaceutically acceptable salt thereof, (c) a sulfonylurea or pharmaceutically acceptable salt thereof, and (d) a pharmaceutically acceptable excipient.

DETAILED DESCRIPTION OF THE INVENTION

The present invention is directed to methods for the treatment and prevention of glucose related disorders comprising administering to a subject in need thereof a therapeutically effective amount of co-therapy comprising (a) metformin or a pharmaceutically acceptable salt thereof and (b) a compound of formula (I)

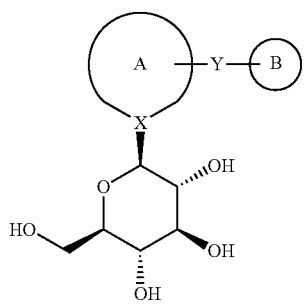

(I)

wherein Ring A, Ring B, X and Y are as herein defined; or pharmaceutically acceptable salt thereof.

The compounds of the formula (I) exhibit an inhibitory activity against sodium-dependent glucose transporter, such as for example SGLT2. The compounds of formula (I) exhibit an inhibitory activity against sodium-dependent glucose transporter, present in the intestine and the kidney of mammalian species, and further exhibit a blood glucose lowering effect. The compounds of formula (I) may be prepared according to the process as disclosed in Nomura, S. et al., US Patent Publication, US 2005/0233988 A1, published Oct. 20, 2005, which is incorporated by reference herein.

In an embodiment, the present invention is directed to methods for the treatment and prevention of glucose related disorders comprising administering to a subject in need thereof a therapeutically effective amount of co-therapy comprising (a) metformin or a pharmaceutically acceptable salt thereof and (b) a compound of formula (I-X)

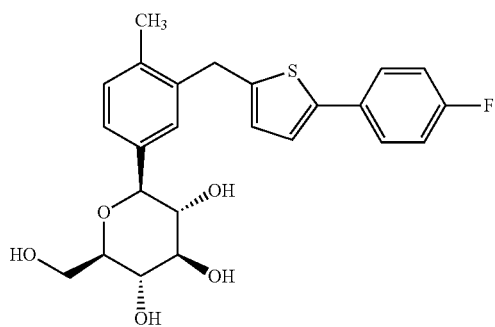

(I-X)

or pharmaceutically acceptable salt thereof. In certain preferred embodiments, the compound of formula (I-X) is the crystalline form of the hemihydrate of the compound of Formula (I-X), as described in WO 2008/069327, the disclosure of which is hereby incorporated by reference in its entirety.

In another embodiment, the present invention is directed to methods for the treatment and prevention of glucose related disorders comprising administering to a subject in need thereof a therapeutically effective amount of co-therapy comprising (a) metformin or a pharmaceutically acceptable salt thereof and (b) a compound of formula (I-Y)

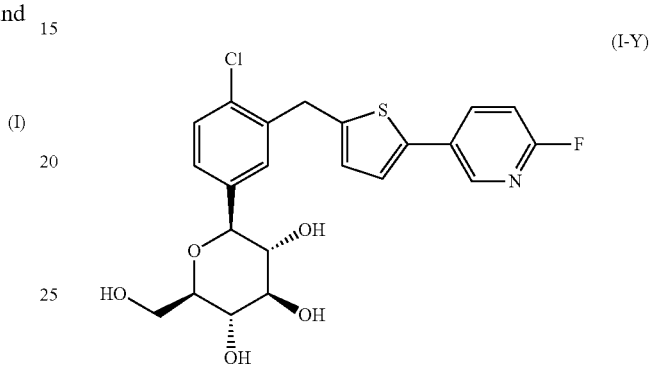

(I-Y)

or pharmaceutically acceptable salt thereof.

The present invention is further directed to methods for the treatment and prevention of glucose related disorders comprising administering to a subject in need thereof a therapeutically effective amount of co-therapy comprising (a) a sulfonylurea (preferably glyburide) or a pharmaceutically acceptable salt thereof, and (b) a compound of formula (I)

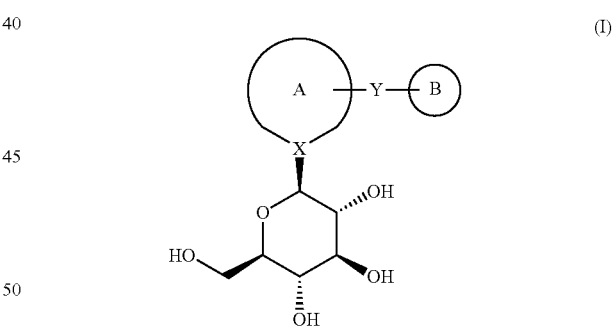

(I)

wherein Ring A, Ring B, X and Y are as herein defined; or pharmaceutically acceptable salt thereof. In another embodiment, the present invention is directed to methods for the treatment and prevention of glucose related disorders comprising administering to a subject in need thereof a therapeutically effective amount of co-therapy comprising (a) a sulfonylurea (preferably glyburide) or a pharmaceutically acceptable salt thereof, and (b) a compound of formula (I-X) or pharmaceutically acceptable salt thereof. In another embodiment, the present invention is directed to methods for the treatment and prevention of glucose related disorders comprising administering to a subject in need thereof a therapeutically effective amount of co-therapy comprising (a) a sulfonylurea (preferably glyburide) or a pharmaceutically acceptable salt thereof, and (b) a compound of formula (I-Y) or pharmaceutically acceptable salt thereof.

Metformin and more particularly metformin hydrochloride, (also known by the trade names GLUCOPHAGE, RIOMET, FORTAMET, GLUMETZA, OBIMET, DIANBEN, DIABEX, DIAFORMIN, and others) is an oral antidiabetic drug of the biguanide class. Metformin is a first-line therapy for Type 2 diabetes mellitus, particularly in overweight and obese people. The usual starting dose of metformin (for example, as metformin hydrochloride tablets) in the United States and certain other countries is 500 mg twice a day or 850 mg once a day, given with meals. The daily dosage may be increases in increments of 500 mg weekly or 850 mg every 2 weeks, up to a total of 2000 mg per day, given in divided doses. Patients can also be titrated from 500 mg twice a day to 850 mg twice a day after 2 weeks. For those patients requiring additional glycemic control, metformin may be given to a maximum daily dose of 2550 mg per day. Doses above 2000 mg may be better tolerated given three times a day with meals. Preferably, the metformin or pharmaceutically acceptable salt thereof is metformin hydrochloride.

Glyburide (also known as glibenclamide, and further known by the trade names DIABETA, GLYNASE PRESTAB, MICRONASE and others) is an oral anti-diabetic of the sulfonylurea class. Glyburide is used for the treatment of Type II diabetes mellitus and works by inhibiting ATP-sensitive potassium channels in pancreatic beta cells. This inhibition causes cell membrane depolarization, which causes voltage-dependent calcium channels to open, which in turn causes an increase in intracellular calcium in the beta cell, which stimulates insulin release. The starting dosage for glyburide is typically 2.5 mg to 5 mg (1.5 gm to 3 mg, if administered as micronized glyburide) taken daily with meals. As needed, glyburide dosages may be gradually increased (in steps of 2.5 mg or less per week) up to 20 mg daily (or up to 12 mg daily if administered as micronized glyburide). Glyburide may also be administered in combination with metformin, and is available as in combination with metformin under the trade names GLUCOVANCE and GLIBOMET.

The present invention is further directed to methods for the treatment and prevention of glucose related disorders comprising administering to a subject in need thereof a therapeutically effective amount of co-therapy comprising (a) metformin or a pharmaceutically acceptable salt thereof and (b) a compound of formula (I) or pharmaceutically acceptable salt thereof, and (c) a sulfonylurea or pharmaceutically acceptable salt thereof.

In an embodiment, the present invention is directed to methods for the treatment and prevention of glucose related disorders comprising administering to a subject in need thereof a therapeutically effective amount of co-therapy comprising (a) metformin or a pharmaceutically acceptable salt thereof and (b) a compound of formula (I-X) or pharmaceutically acceptable salt thereof, and (c) a sulfonylurea or pharmaceutically acceptable salt thereof.

In another embodiment, the present invention is directed to methods for the treatment and prevention of glucose related disorders comprising administering to a subject in need thereof a therapeutically effective amount of co-therapy comprising (a) metformin or a pharmaceutically acceptable salt thereof and (b) a compound of formula (I-Y) or pharmaceutically acceptable salt thereof, and (c) a sulfonylurea or pharmaceutically acceptable salt thereof.

The present invention is further directed to methods for the treatment and prevention of glucose related disorders comprising administering to a subject in need thereof a therapeutically effective amount of co-therapy comprising (a) metformin or a pharmaceutically acceptable salt thereof and (b) a compound of formula (I) or pharmaceutically acceptable salt thereof, and (c) glyburide.

In another embodiment, the present invention is directed to methods for the treatment and prevention of glucose related disorders comprising administering to a subject in need thereof a therapeutically effective amount of co-therapy comprising (a) metformin or a pharmaceutically acceptable salt thereof and (b) a compound of formula (I-X) or pharmaceutically acceptable salt thereof, and (c) glyburide.

In another embodiment, the present invention is directed to methods for the treatment and prevention of glucose related disorders comprising administering to a subject in need thereof a therapeutically effective amount of co-therapy comprising (a) metformin or a pharmaceutically acceptable salt thereof and (b) a compound of formula (I-Y) or pharmaceutically acceptable salt thereof, and (c) glyburide.

Sulfonylureas are a class of pharmaceutical compounds which increase insulin production by stimulating pancreatic beta cells, and therefore act as insulin secretagogues. The primary mechanism of action of sulfonylureas is to close ATP-sensitive potassium channels in the beta-cell plasma membrane, initiating a chain of events that result in insulin release. Suitable examples of sulfonylureas include, but are not limited to chlorpropamide, tolazamide, tolbutamide, glyburide, glipizide, glimepiride, and like. One skilled in the art can readily determine dosages and regimens for the administration of sulfonylureas, for example by consulting the PDR (Physician's Desk Reference) and/or the FDA required drug literature included with the pharmaceutical agent. For example, a representative dosage for chlorpropamide (DIABINESE®) is 100-250 mg QD; for tolazamide (TOLINASE®) is 250 mg QD or BID; for tolbutamide (ORINASE®) is 1000 mg BID or TID; for glimepiride (AMARYL®) is 2 mg QD; for glipizide (GLUCOTROL®) is 5-10 mg QD or BID; and for glyburide (DIABETA®, MICRONASE®) is 2.5-5 mg QD or BID.

In an embodiment of the present invention, the sulfonylurea is selected from the group consisting of chlorpropamide, tolazamide and tolbutamide; wherein the sulfonylurea is present in (administered in) an amount in the range of from about 100 mg to about 3000 mg, or any amount or range therein, preferably in an amount in the range of from about 100 mg to about 1000 mg, or any amount or range therein. In another embodiment of the present invention, the sulfonylurea is selected from the group consisting of glyburide, glipizide and glimepiride; and is present in an amount in the range of from about 0.1 mg to about 50 mg, or any amount or range therein, preferably in an amount in the range of from about 1.0 mg to about 50 mg, more preferably in an amount in the range of from about 2.0 mg to about 25 mg, or any amount or range therein.

In another embodiment of the present invention, the sulfonylurea is glyburide; wherein the glyburide is present in (administered in) an amount in the range of from about 1.0 mg to about 20 mg daily, or any amount or range therein; preferably in an amount in the range of from about 2.5 mg to about 20 mg, daily, or any amount or range therein, more preferably in an amount in the range of from about 2.5 mg to about 10 mg daily, or any amount or range therein, more preferably in an amount in the range of from about 2.5 mg to about 5 mg daily, or any amount or range therein.

The present invention is further directed to a pharmaceutical composition comprising a therapeutically effective amount of co-therapy comprising (a) metformin or a pharmaceutically acceptable salt thereof; and (b) a compound of formula (I) or pharmaceutically acceptable salt thereof. The present invention is further directed to a pharmaceutical composition comprising a therapeutically effective amount of co-therapy comprising (a) glyburide; and (b) a compound of formula (I) or pharmaceutically acceptable salt thereof.

The present invention is further directed to a pharmaceutical composition comprising a therapeutically effective amount of co-therapy comprising (a) metformin or a pharmaceutically acceptable salt thereof; (b) a compound of formula (I) or pharmaceutically acceptable salt thereof, and (c) a sulfonylurea or pharmaceutically acceptable salt thereof.

In an embodiment, the present invention is directed to a pharmaceutical composition comprising (a) metformin or a pharmaceutically acceptable salt thereof and (b) a compound of formula (I-X) or pharmaceutically acceptable salt thereof. In another embodiment, the present invention is directed to a pharmaceutical composition comprising (a) metformin or a pharmaceutically acceptable salt thereof and (b) a compound of formula (I-Y) or pharmaceutically acceptable salt thereof. In another embodiment of the present invention, the pharmaceutical composition is an immediate release dosage form. In another embodiment of the present invention, the pharmaceutical composition is an extended release dosage form, wherein the dosage form releases the one or more of the active ingredients over a period of time in the range of from about 8 to about 24 hours, or any amount or range therein.

In an embodiment, the present invention is directed to a pharmaceutical composition comprising (a) glyburide and (b) a compound of formula (I-X) or pharmaceutically acceptable salt thereof. In another embodiment, the present invention is directed to a pharmaceutical composition comprising (a) glyburide and (b) a compound of formula (I-Y) or pharmaceutically acceptable salt thereof. In another embodiment of the present invention, said pharmaceutical composition is an immediate release dosage form. In another embodiment of the present invention, the pharmaceutical composition is an extended release dosage form, wherein the dosage form releases the one or more of the active ingredients over a period of time in the range of from about 8 to about 24 hours, or any amount or range therein.

In an embodiment, the present invention is directed to a pharmaceutical composition comprising (a) metformin or a pharmaceutically acceptable salt thereof, (b) a compound of formula (I-X) or pharmaceutically acceptable salt thereof, and (c) a sulfonylurea or pharmaceutically acceptable salt thereof. In another embodiment, the present invention is directed to a pharmaceutical composition comprising (a) metformin or a pharmaceutically acceptable salt thereof, (b) a compound of formula (I-Y) or pharmaceutically acceptable salt thereof, and (c) a sulfonylurea or pharmaceutically acceptable salt thereof. In another embodiment of the present invention, the pharmaceutical composition is an immediate release dosage form. In another embodiment of the present invention, the pharmaceutical composition is an extended release dosage form, wherein the dosage form releases one or more of the active ingredients over a period of time in the range of from about 8 to about 24 hours, or any amount or range therein, preferably over a time in the range of from about 8 hours to about 12 hours, or any amount or range therein.

In an embodiment, the present invention is directed to a pharmaceutical composition wherein the metformin or pharmaceutically acceptable salt thereof is metformin hydrochloride. In another embodiment, the present invention is directed to a pharmaceutical composition wherein the metformin hydrochloride is present at a dosage amount in the range of from about 100 mg to about 2000 mg, preferably from about 250 mg to about 2000 mg, preferably from about 250 mg to about 1000 mg, or any amount or range therein. In another embodiment, the present invention is directed to a pharmaceutical composition wherein the metformin hydrochloride is present at a dosage amount selected from the group consisting of 250 mg, 500 mg, 750 mg, 850 mg, 1000 mg, 1700 mg and 2000 mg.

In an embodiment, the present invention is directed to a pharmaceutical composition wherein the glyburide is present at a dosage amount in the range of from about 1.0 mg to about 20.0 mg, preferably from about 2.5 mg to about 20.0 mg, more preferably from about 2.5 mg to about 10.0 mg, or any amount or range therein. In another embodiment, the present invention is directed to a pharmaceutical composition wherein the glyburide is present at a dosage amount selected from the group consisting of 1.0, 1.5, 2.5, 5.0, 7.5, 10, 12.5, 15 and 20 mg.

In an embodiment, the present invention is directed to a pharmaceutical composition wherein the compound of formula (I) or pharmaceutically acceptable salt thereof is selected from the group consisting of a compound of formula (I-X) or pharmaceutically acceptable salt thereof; and a compound of formula (I-Y) or pharmaceutically acceptable salt thereof. In another embodiment, the present invention is directed to a pharmaceutical composition wherein the compound of formula (I) or pharmaceutically acceptable salt thereof is the compound of formula (I-X) or pharmaceutically acceptable salt thereof.

In another embodiment, the present invention is directed to a pharmaceutical composition wherein the compound of formula (I-X) or pharmaceutically acceptable salt thereof is present at a dosage amount in the range of from about 1 mg to about 500 mg, preferably from about 1 mg to about 300 mg, preferably from about 25 mg to about 300 mg, or any amount or range therein. In another embodiment, the present invention is directed to a pharmaceutical composition wherein the compound of formula (I-X) or pharmaceutically acceptable salt thereof is present at a dosage amount in the range of from about 25 mg to about 300 mg, preferably selected from the group consisting of 50 mg, 100 mg, 150 mg, 200 mg and 300 mg.

In another embodiment, the present invention is directed to a pharmaceutical composition wherein the compound of formula (I-Y) or pharmaceutically acceptable salt thereof is present at a dosage amount in the range of from 1 mg to about 500 mg, preferably from about 1 mg to about 100 mg, or from about 1 mg to about 50 mg, or any amount or range therein. In another embodiment, the present invention is directed to a pharmaceutical composition wherein the compound of formula (I-Y) or pharmaceutically acceptable salt thereof is present at a dosage amount selected from the group consisting of 1 mg, 5 mg, 10 mg, 25 mg, 50 mg and 100 mg.

In yet another embodiment, the present invention is directed to a pharmaceutical composition comprising:
(a) metformin or a pharmaceutically acceptable salt thereof;
(b) a compound of formula (I) or pharmaceutically acceptable salt thereof selected from the group consisting of a compound of formula (I-X) or pharmaceutically acceptable salt thereof; and a compound of formula (I-Y) or pharmaceutically acceptable salt thereof;

wherein the metformin or pharmaceutically acceptable salt thereof is present in an amount in the range of from about 100 mg to about 2000 mg, preferably from about 500 mg to about 1000 mg, or any amount or range therein; and wherein the compound of formula (I) or pharmaceutically acceptable salt thereof is present in an amount in the range of from about 1 mg to about 1000 mg, or any amount or range therein (preferably in an amount in the range of from about 1 mg to about 500 mg, or any amount or range therein, more preferably in an amount in the range of from about 10 mg to about 300 mg, or any amount or range therein).

In yet another embodiment, the present invention is directed to a pharmaceutical composition comprising:

(a) glyburide; wherein the glyburide is present in an amount in the range of from about 1.0 mg to about 20 mg, preferably from about 2.5 mg to about 20 mg, or any amount or range therein; and (b) a compound of formula (I) or pharmaceutically acceptable salt thereof (wherein the compound of formula (I) or pharmaceutically acceptable salt thereof is preferably selected from the group consisting of a compound of formula (I-X) or pharmaceutically acceptable salt thereof; and a compound of formula (I-Y) or pharmaceutically acceptable salt thereof); wherein the compound of formula (I) or pharmaceutically acceptable salt thereof is present in an amount in the range of from about 1 mg to about 1000 mg, or any amount or range therein (preferably in an amount in the range of from about 1 mg to about 500 mg, or any amount or range therein, more preferably in an amount in the range of from about 10 mg to about 300 mg, or any amount or range therein).

In an embodiment of the present invention, the compound of formula (I) is a compound of formula (I-X) and is present in the pharmaceutical composition in an amount in the range of from about 1 mg to about 1000 mg, or any amount or range therein, preferably in an amount in the range of from about 50 mg to about 300 mg, or any amount or range therein. In another embodiment of the present invention, the compound of formula (I) is a compound of formula (I-Y) and is present in the pharmaceutical composition in an amount in the range of from about 1 mg to about 1000 mg, or any amount or range therein, preferably in an amount in the range of from about 1 mg to about 100 mg, or any amount or range therein, more preferably in an amount in the range of from about 10 mg to about 50 mg, or any range thereof.

In yet another embodiment, the present invention is directed to a pharmaceutical composition comprising:

(a) metformin or a pharmaceutically acceptable salt thereof; wherein the metformin or pharmaceutically acceptable salt thereof is present in an amount in the range of from about 100 mg to about 2000 mg, preferably from about 500 mg or about 1000 mg, or any amount or range therein;

(b) a compound of formula (I) or pharmaceutically acceptable salt thereof (wherein the compound of formula (I) is preferably selected from the group consisting of a compound of formula (I-X) or pharmaceutically acceptable salt thereof; and a compound of formula (I-Y) or pharmaceutically acceptable salt thereof); wherein the compound of formula (I) or pharmaceutically acceptable salt thereof is present in an amount in the range of from about 1 mg to about 1000 mg, or any amount or range therein (preferably in an amount in the range of from about 1 mg to about 500 mg, or any amount or range therein, more preferably in an amount in the range of from about 10 mg to about 300 mg, or any amount or range therein); and and (c) glyburide; wherein the glyburide is present in an amount in the range of from about 1.0 mg to about 20 mg, preferably from about 2.5 mg to about 20 mg, or any amount or range therein.

In an embodiment, the present invention is directed to a pharmaceutical composition comprising (a) metformin hydrochloride; (b) a compound of formula (I) or pharmaceutically acceptable salt thereof selected from the group consisting of a compound of formula (I-X) or pharmaceutically acceptable salt thereof; and a compound of formula (I-Y) or pharmaceutically acceptable salt thereof; and one or more pharmaceutically acceptable excipients. The pharmaceutically acceptable excipients, include but are not limited to, disintegrants, binders, diluents, lubricants, stabilizers, antioxidants, surfactants, colorants, plasticizers, coatings and the like. More particularly, suitable pharmaceutical excipients comprise one or more of the following: (i) diluents such as lactose, microcrystalline cellulose, dicalcium phosphate, starch and the like; (ii) binders such as polyvinylpyrrolidone (such as POVIDONE), methylcellulose, hydroxypropyl cellulose, hydroxypropyl methylcellulose (such as METHOCEL™ E-5), and the like; (iii) disintegrants such as sodium starch glycolate, croscamellose sodium, crospovidone and the like; (iv) wetting agents such as surfactants, such as sodium lauryl stearate, polysorbate 20, and the like; (v) lubricants such as magnesium stearate, sodium stearyl fumarate, talc, and the like; (vi) flow promoters or glidants such as colloidal silicon dioxide, talc and the like; and other excipients known to be useful in the preparation of pharmaceutical compositions. Additional suitable pharmaceutical excipients and their properties may be found in texts such as *Handbook of Pharmaceutical Excipients*, Edited by R. C. Rowe, P. J. Sheskey & P. J. Weller, Fourth Edition (Published by Pharmaceutical Press, a Division of Royal Pharmaceutical Society of Great Britain). In another embodiment, the present invention is directed to a pharmaceutical composition as described above, further comprising a sulfonylurea or pharmaceutically acceptable salt thereof.

Fillers or diluents for use in the pharmaceutical compositions of the present invention include fillers or diluents typically used in the formulation of pharmaceuticals. Examples of fillers or diluents for use in accordance with the present invention include but are not limited to sugars such as lactose, dextrose, glucose, sucrose, cellulose, starches and carbohydrate derivatives, polysaccharides (including dextrates and maltodextrin), polyols (including mannitol, xylitol, and sorbitol), cyclodextrins, calcium carbonates, magnesium carbonates, microcrystalline cellulose, combinations thereof, and the like.

Binders for use in the pharmaceutical compositions of the present invention include binders commonly used in the formulation of pharmaceuticals. Examples of binders for use in accordance with the present invention include but are not limited to cellulose derivatives (including hydroxypropyl cellulose, hydroxypropyl methylcellulose, methylcellulose, and sodium carboxymethyl cellulose), glycol, sucrose, dextrose, corn syrup, polysaccharides (including acacia, targacanth, guar, alginates and starch), corn starch, pregelatinized starch, modified corn starch, gelatin, polyvinylpyrrolidone, polyethylene, polyethylene glycol, combinations thereof and the like.

Disintegrants for use in the pharmaceutical compositions of the present invention include disintegrants commonly used in the formulation of pharmaceuticals. Examples of disintegrants for use in accordance with the present invention include but are not limited to starches, and crosslinked starches, celluloses and polymers, combinations thereof and the like. Representative disintegrants include microcrystalline cellulose, croscarmellose sodium, alginic acid, sodium alginate, crosprovidone, cellulose, agar and related gums, sodium starch glycolate, corn starch, potato starch, sodium starch glycolate, Veegum HV, methylcellulose, agar, bentonite, sodium carboxymethylcellulose, calcium carboxymethylcellulose, carboxymethylcellulose, alginic acid, guar gum combinations thereof, and the like.

Lubricants, glidants or anti-tacking agents for use in the pharmaceutical compositions of the present invention include lubricants, glidants and anti-tacking agents commonly used in the formulation of pharmaceuticals. Examples for use in accordance with the present invention include but are not limited to magnesium carbonate, magnesium laurylsulphate, calcium silicate, talc, fumed silicon dioxide, combinations thereof, and the like. Other useful lubricants include but are not limited to magnesium stearate, calcium stearate, stearic acid, sodium stearyl fumarate, polyethylene glycol, sodium lauryl sulphate, magnesium lauryl sulphate, sodium benzoate, colloidal silicon dioxide, magnesium oxide, magnesium silicate, mineral oil, hydrogenated vegetable oils, waxes, glyceryl behenate, polyethylene glycol, and combinations thereof, and the like.

Surfactants for use in the pharmaceutical compositions of the present invention include surfactants commonly used in the formulation of pharmaceuticals. Examples of surfactants for use in accordance with the present invention include but are not limited to ionic- and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, phospholipids, combinations thereof, and the like.

Other polymers commonly used as excipients in pharmaceutical compositions include, but are not limited to, methylcellulose (MC), ethylcellulose (EC), hydroxyethylcellulose (HEC), methyl hydroxyethylcellulose (MHEC), hydroxypropyl cellulose (HPC), hydroxypropyl methylcellulose (HPMC), sodium carboxymethylcellulose (NaCMC), and the like.

The pharmaceutical compositions can further comprise antioxidants and chelating agents. For example, the pharmaceutical formulations can comprise butylated hydroxyanisole (BHA), butylated hydroxytoluene (BHT), propyl gallate (PG), sodium metabisulfite, ascorbyl palmitate, potassium metabisulfite, disodium EDTA (ethylenediamine tetraacetic acid; also known as disodium edentate), EDTA, tartaric acid, citric acid, citric acid monohydrate, and sodium sulfite.

The pharmaceutical compositions may further optionally comprise one or more flow regulators (or glidants). Flow regulators may be present in powders or granules and are admixed in order to increase their flowability of the composition during manufacture, particularly in the preparation of tablets produced by pressing powders or granules. Flow regulators which can be employed include, but are not limited to, highly disperse silicon dioxide (Aerosil) or dried starch.

One skilled in the art will readily recognize that the appropriate pharmaceutically acceptable excipients are selected such that they are compatible with other excipients and do not bind with the drug compound(s) (active ingredient(s)) or cause drug degradation.

Tablet compositions may further optionally comprise a coating. Suitable coatings include, but are not limited to, film-forming polymers, such as, for example, those from the group of the cellulose derivatives, dextrins, starches, natural gums, such as, for example, gum arabic, xanthans, alginates, polyvinyl alcohol, polymethacrylates and derivatives thereof, such as, for example, Eudragit®; which may be applied to the tablet as solutions or suspensions by means of the various pharmaceutical conventional methods, such as, for example, film coating. The coating is typically applied as a solutions/suspensions which, in addition to any film-forming polymer present, may further comprise one or more adjuvants, such as hydrophilisers, plasticisers, surfactants, dyes and white pigments, such as, for example, titanium dioxide.

In certain embodiments of the present invention, the pharmaceutical composition preferably comprising between about 5% and about 50% by weight of diluents (relative to the total weight of the composition or composition layer), more preferably between about 5% and about 25% by weight diluent, more preferably still about 7% diluent.

In additional embodiments of the present invention, the pharmaceutical composition preferably comprising between about 1% and about 10% by weight of binder (relative to the total weight of the composition or composition layer), more preferably between about 3% and about 5% by weight binder, more preferably still about 4% binder.

In additional embodiments of the present invention, the pharmaceutical composition preferably comprising between about 1% and about 10% by weight of disintegrant (relative to the total weight of the composition or composition layer), more preferably between about 2% and about 5% by weight disintegrant, more preferably still about 3% disintegrant.

In additional embodiments of the present invention, the pharmaceutical composition preferably comprising between about 0% and about 5% by weight of wetting agent (relative to the total weight of the composition or composition layer), more preferably between about 0.1% and about 2% by weight wetting agent, more preferably still about 0.3% wetting agent.

In additional embodiments of the present invention, the pharmaceutical composition preferably comprising between about 0% and about 3% by weight of lubricant (relative to the total weight of the composition or composition layer), more preferably between about 0.1% and about 2% by weight lubricant, more preferably still about 0.5% lubricant.

Definitions

The term "halogen atom" or "halo" means chlorine, bromine, fluorine and iodine, and chlorine and fluorine are preferable.

The term "alkyl group" means a straight or branched saturated monovalent hydrocarbon chain having 1 to 12 carbon atoms. The straight chain or branched chain alkyl group having 1 to 6 carbon atoms is preferable, and the straight chain or branched chain alkyl group having 1 to 4 carbon atoms is more preferable. Examples thereof are methyl group, ethyl group, propyl group, isopropyl group, butyl group, t-butyl group, isobutyl group, pentyl group, hexyl group, isohexyl group, heptyl group, 4,4-dimethylpentyl group, octyl group, 2,2,4-trimethylpentyl group, nonyl group, decyl group, and various branched chain isomers thereof. Further, the alkyl group may optionally and independently be substituted by 1 to 4 substituents as listed below, if necessary.

The term "alkylene group" or "alkylene" means a straight or branched divalent saturated hydrocarbon chain having 1 to 12 carbon atoms. The straight chain or branched chain alkylene group having 1 to 6 carbon atoms is preferable, and the straight chain or branched chain alkylene group having 1 to 4 carbon atoms is more preferable. Examples thereof are methylene group, ethylene group, propylene group, trimethylene group, etc. If necessary, the alkylene group may optionally be substituted in the same manner as the above-mentioned "alkyl group". Where alkylene groups as defined above attach at two different carbon atoms of the benzene ring, they form an annelated five, six or seven membered carbocycle together with the carbon atoms to which they are attached, and may optionally be substituted by one or more substituents defined below.

The term "alkenyl group" means a straight or branched monovalent hydrocarbon chain having 2 to 12 carbon atoms and having at least one double bond. Preferable alkenyl group is a straight chain or branched chain alkenyl group having 2 to 6 carbon atoms, and the straight chain or branched chain alkenyl group having 2 to 4 carbon atoms is more preferable. Examples thereof are vinyl group, 2-propenyl group, 3-butenyl group, 2-butenyl group, 4-pentenyl group, 3-pentenyl group, 2-hexenyl group, 3-hexenyl group, 2-heptenyl group, 3-heptenyl group, 4-heptenyl group, 3-octenyl group, 3-nonenyl group, 4-decenyl group, 3-undecenyl group, 4-dodecenyl group, 4,8,12-tetradecatrienyl group, etc. The alkenyl group may optionally and independently be substituted by 1 to 4 substituents as mentioned below, if necessary.

The term "alkenylene group" means a straight or branched divalent hydrocarbon chain having 2 to 12 carbon atoms and having at least one double bond. The straight chain or branched chain alkenylene group having 2 to 6 carbon atoms is preferable, and the straight chain or branched chain alkenylene group having 2 to 4 carbon atoms is more preferable. Examples thereof are vinylene group, propenylene group, butadienylene group, etc. If necessary, the alkylene group may optionally be substituted by 1 to 4 substituents as mentioned below, if necessary. Where alkenylene groups as defined above attach at two different carbon atoms of the benzene ring, they form an annelated five, six or seven membered carbocycle (e.g., a fused benzene ring) together with the carbon atoms to which they are attached, and may optionally be substituted by one or more substituents defined below.

The term "alkynyl group" means a straight or branched monovalent hydrocarbon chain having at least one triple bond. The preferable alkynyl group is a straight chain or branched chain alkynyl group having 2 to 6 carbon atoms, and the straight chain or branched chain alkynyl group having 2 to 4 carbon atoms is more preferable. Examples thereof are 2-propynyl group, 3-butynyl group, 2-butynyl group, 4-pentynyl group, 3-pentynyl group, 2-hexynyl group, 3-hexynyl group, 2-heptynyl group, 3-heptynyl group, 4-heptynyl group, 3-octynyl group, 3-nonynyl group, 4-decynyl group, 3-undecynyl group, 4-dodecynyl group, etc. The alkynyl group may optionally and independently be substituted by 1 to 4 substituents as mentioned below, if necessary.

The term "cycloalkyl group" means a monocyclic or bicyclic monovalent saturated hydrocarbon ring having 3 to 12 carbon atoms, and the monocyclic saturated hydrocarbon group having 3 to 7 carbon atoms is more preferable. Examples thereof are a monocyclic alkyl group and a bicyclic alkyl group such as cyclopropyl group, cyclobutyl group, cyclopentyl group, cyclohexyl group, cycloheptyl group, cyclooctyl group, cyclodecyl group, etc. These groups may optionally and independently be substituted by 1 to 4 substituents as mentioned below, if necessary. The cycloalkyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the condensed unsaturated hydrocarbon ring may be optionally and independently be substituted by 1 to 4 substituents as mentioned below.

The term "cycloalkylidene group" means a monocyclic or bicyclic divalent saturated hydrocarbon ring having 3 to 12 carbon atoms, and the monocyclic saturated hydrocarbon group having 3 to 6 carbon atoms is preferable. Examples thereof are a monocyclic alkylidene group and a bicyclic alkylidene group such as cyclopropylidene group, cyclobutylidene group, cyclopentylidine group, cyclohexylidene group, etc. These groups may optionally and independently be substituted by 1 to 4 substituents as mentioned below, if necessary. Besides, the cycloalkylidene group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkenyl group" means a monocyclic or bicyclic monovalent unsaturated hydrocarbon ring having 4 to 12 carbon atoms and having at least one double bond. The preferable cycloalkenyl group is a monocyclic unsaturated hydrocarbon group having 4 to 7 carbon atoms. Examples thereof are monocyclic alkenyl groups such as cyclopentenyl group, cyclopentadienyl group, cyclohexenyl group, etc. These groups may optionally and independently be substituted by 1 to 4 substituents as mentioned below, if necessary. Besides, the cycloalkenyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkynyl group" means a monocyclic or bicyclic unsaturated hydrocarbon ring having 6 to 12 carbon atoms, and having at least one triple bond. The preferable cycloalkynyl group is a monocyclic unsaturated hydrocarbon group having 6 to 8 carbon atoms. Examples thereof are monocyclic alkynyl groups such as cyclooctynyl group, cyclodecynyl group. These groups may optionally be substituted by 1 to 4 substituents as mentioned below, if necessary. Besides, the cycloalkynyl group may optionally and independently be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "aryl group" means a monocyclic or bicyclic monovalent aromatic hydrocarbon group having 6 to 10 carbon atoms. Examples thereof are phenyl group, naphthyl group (including 1-naphthyl group and 2-naphthyl group). These groups may optionally and independently be substituted by 1 to 4 substituents as mentioned below, if necessary. Besides, the aryl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "unsaturated monocyclic heterocyclic ring" means an unsaturated hydrocarbon ring containing 1-4 heteroatoms independently selected from a nitrogen atom, an oxygen atom and a sulfur atom, and the preferable one is a 4- to 7-membered saturated or unsaturated hydrocarbon ring containing 1-4 heteroatoms independently selected from a nitrogen atom, an oxygen atom and a sulfur atom. Examples thereof are pyridine, pyrimidine, pyrazine, furan, thiophene, pyrrole, imidazole, pyrazole, oxazole, isoxazole, 4,5-dihydrooxazole, thiazole, isothiazole, thiadiazole, triazole, tetrazole, etc. Among them, pyridine, pyrimidine, pyrazine, furan, thiophene, pyrrole, imidazole, oxazole, and thiazole can be preferably used. The "unsaturated monocyclic heterocyclic ring" may optionally and independently be substituted by 1-4 substituents as mentioned below, if necessary.

The term "unsaturated fused heterobicyclic ring" means hydrocarbon ring comprised of a saturated or a unsaturated hydrocarbon ring condensed with the above mentioned unsaturated monocyclic heterocyclic ring where said saturated hydrocarbon ring and said unsaturated hydrocarbon ring may optionally contain an oxygen atom, a nitrogen atom, a sulfur atom, SO, or $SO_2$ within the ring, if necessary. The "unsaturated fused heterobicyclic ring" includes, for example, benzothiophene, indole, tetrahydrobenzothiophene, benzofuran, isoquinoline, thienothiophene, thienopyridine, quinoline, indoline, isoindoline, benzothiazole, benzoxazole, indazole, dihydroisoquinoline, etc. Further, the "heterocyclic ring" also includes possible N- or S-oxides thereof.

The term "heterocyclyl" means a monovalent group of the above-mentioned unsaturated monocyclic heterocyclic ring or unsaturated fused heterobicyclic ring and a monovalent group of the saturated version of the above-mentioned unsaturated monocyclic heterocyclic or unsaturated fused heterobicyclic ring. If necessary, the heterocyclyl may optionally and independently be substituted by 1 to 4 substituents as mentioned below.

The term "alkanoyl group" means a formyl group and ones formed by binding an "alkyl group" to a carbonyl group.

The term "alkoxy group" means ones formed by binding an "alkyl group" to an oxygen atom.

The substituent for the above each group includes, for example, a halogen atom (e.g., fluorine, chlorine, bromine, iodine), a nitro group, a cyano group, an oxo group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyl-oxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a hetero-cyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxy-carbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkyl-carbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group. Each group as mentioned above may optionally be substituted by these substituents.

Further, the terms such as a haloalkyl group, a halo-lower alkyl group, a haloalkoxy group, a halo-lower alkoxy group, a halophenyl group, or a haloheterocyclyl group mean an alkyl group, a lower alkyl group, an alkoxy group, a lower alkoxy group, a phenyl group or a heterocyclyl group (hereinafter, referred to as an alkyl group, etc.) being substituted by one or more halogen atoms, respectively. Preferable ones are an alkyl group, etc. being substituted by 1 to 7 halogen atoms, and more preferable ones are an alkyl group, etc. being substituted by 1 to 5 halogen atoms. Similarly, the terms such as a hydroxyalkyl group, a hydroxy-lower alkyl group, a hydroxyalkoxy group, a hydroxy-lower alkoxy group and a hydroxyphenyl group mean an alkyl group, etc., being substituted by one or more hydroxy groups. Preferable ones are an alkyl group, etc., being substituted by 1 to 4 hydroxy groups, and more preferable ones are an alkyl group, etc., being substituted by 1 to 2 hydroxy groups. Further, the terms such as an alkoxyalkyl group, a lower alkoxyalkyl group, an alkoxy-lower alkyl group, a lower alkoxy-lower alkyl group, an alkoxyalkoxy group, a lower alkoxyalkoxy group, an alkoxy-lower alkoxy group, a lower alkoxy-lower alkoxy group, an alkoxyphenyl group, and a lower alkoxyphenyl group means an alkyl group, etc., being substituted by one or more alkoxy groups. Preferable ones are an alkyl group, etc., being substituted by 1 to 4 alkoxy groups, and more preferable ones are an alkyl group, etc., being substituted by 1 to 2 alkoxy groups.

The terms "arylakyl" and "arylalkoxy" as used alone or as part of another group refer to alkyl and alkoxy groups as described above having an aryl substituent.

The term "lower" used in the definitions for the formulae in the present specification means a straight or branched carbon chain having 1 to 6 carbon atoms, unless defined otherwise. More preferably, it means a straight or branched carbon chain having 1 to 4 carbon atoms.

Examples of the optionally substituted unsaturated monocyclic heterocyclic ring of the present invention include an unsaturated monocyclic heterocyclic ring which may optionally be substituted by 1-5 substituents selected from the group consisting of a halogen atom, a nitro group, a cyano group, an oxo group, a hydroxyl group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl wherein each substituent may optionally be further substituted by these substituents.

Examples of the optionally substituted unsaturated fused heterobicyclic ring of the present invention include an unsaturated fused heterobicyclic ring which may optionally be substituted by 1-5 substituents selected from the group consisting of a halogen atom, a nitro group, a cyano group, an oxo group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenyl-carbonyl group, a cycloalkynyl-carbonyl group, an arylcarbonyl group, a heterocyclylcarbonyl group, an alkoxycarbonyl group, an alkenyloxycarbonyl group, an alkynyloxy-carbonyl group, a cycloalkyloxycarbonyl group, a cycloalkenyloxy-carbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cyclo-alkylcarbonyloxy group, a cycloalkenylcarbonyloxy group, a cyclo-alkynylcarbonyloxy group, an arylcarbonyloxy group, a heterocyclyl-carbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoyl-amino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cyclo-alkenylsulfonyl group, a cycloalkynylsulfonyl group, an arylsulfonyl group, and a heterocyclylsulfonyl group, wherein each substituent may optionally be further substituted by these substituents.

Examples of the optionally substituted benzene ring of the present invention include a benzene ring which may optionally be substituted by 1-5 substituents selected from the group consisting of a halogen atom, a nitro group, a cyano group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyl-oxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, a heterocyclylsulfonyl group, an alkylene group, an alkyleneoxy group, an alkylenedioxy group, and an alkenylene group wherein each substituent may optionally be further substituted by these substituents. Moreover, examples of the optionally substituted benzene ring include a benzene ring substituted with an alkylene group to form an annelated carbocycle together with the carbon atoms to which they are attached, and also includes a benzene ring substituted with an alkenylene group to form an annelated carbocycle such as a fused benzene ring together with the carbon atoms to which they are attached.

Preferable examples of the optionally substituted unsaturated monocyclic heterocyclic ring include an unsaturated monocyclic heterocyclic ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted unsaturated fused heterobicyclic ring include an unsaturated fused heterobicyclic ring which may optionally be substituted by 1-3 substituents independently selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cyclo-alkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted benzene ring include a benzene ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, an alkylene group, an alkyleneoxy group, an alkylenedioxy group, and an alkenylene group.

Preferably, the optionally substituted unsaturated monocyclic heterocyclic ring is an unsaturated monocyclic heterocyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsufonylamino group, a phenyl group, a phenoxy group, a phenylsulfonylamino group, a phenylsulfonyl group, a heterocyclyl group, and an oxo group;

the optionally substituted unsaturated fused heterobicyclic ring is an unsaturated fused heterobicyclic ring which may optionally be substituted by 1-3 substituents selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkyl-sulfamoyl group, a carboxyl group, an alkoxycarbonyl group, a carbamoyl group, a mono- or di-alkylcarbamoyl group, an alkanoyl group, an alkylsulfonylamino group, a phenyl group, a phenoxy group, a phenylsulfonylamino group, phenylsulfonyl group, a heterocyclyl group, and an oxo group; and the optionally substituted benzene ring is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsufonylamino group, a phenyl group, a phenoxy group, a phenylsulfonylamino group, a phenylsulfonyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a hydroxy group, a cyano group, an alkyl group, a haloalkyl group, an alkoxy group, a haloalkoxy group, an alkanoyl group, an alkylthio group, an alkylsulfonyl group, a mono- or di-alkylamino group, a carboxyl group, an alkoxycarbonyl group, a phenyl group, an alkyleneoxy group, an alkylenedioxy group, an oxo group, a carbamoyl group, and a mono- or di-alkylcarbamoyl group.

Preferably, the optionally substituted unsaturated monocyclic heterocyclic ring is an unsaturated monocyclic heterocyclic ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, and an oxo group;

the optionally substituted unsaturated fused heterobicyclic ring is an unsaturated fused heterobicyclic ring which may optionally be substituted by 1-3 substituents independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxy group, an alkoxycarbonyl group, a carbamoyl group, a mono- or di-alkylcarbamoyl group, a phenyl group, a heterocyclyl group, and an oxo group; and the optionally substituted benzene ring is a benzene ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In a preferred embodiment of the present invention, in the compound of formula (I), (1) Ring A is an unsaturated monocyclic heterocyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsufonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsufonylamino group, a phenyl group, a phenoxy group, a phenylsulfonylamino group, a phenylsulfonyl group, a heterocyclyl group, an alkylene group, and an alkenylene group;

(2) Ring A is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, an alkanoylamino group, a sulfamoyl group, a mono- or di-alkylsulfamoyl group, a carboxyl group, an alkoxycarbonyl group, a carbamoyl group, a mono- or di-alkylcarbamoyl group, an alkylsufonylamino group, a phenyl group, a phenoxy group, a phenylsulfonylamino group, a phenylsulfonyl group, a heterocyclyl group, an alkylene group, and an alkenylene group, and Ring B is an unsaturated monocyclic heterocyclic ring or an unsaturated fused heterobicyclic ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsufonylamino group, a phenyl group, a phenoxy group, a phenylsulfonylamino group, a phenylsulfonyl group, a heterocyclyl group, an alkylene group and an oxo group; or (3) Ring A is an unsaturated fused heterobicyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsufonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsufonylamino group, a phenyl group, a phenoxy group, a phenylsulfonylamino group, a phenylsulfonyl group, a heterocyclyl group, an alkylene group and an oxo group;

wherein each of the above-mentioned substituents on Ring A and Ring B may optionally be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In another preferred embodiment of the present invention, in the compound of formula (I), Ring A and Ring B are (1) Ring A is an unsaturated monocyclic heterocyclic ring which may optionally be substituted by a halogen atom, a lower alkyl group, a halo-lower alkyl group, a lower alkoxy group, or an oxo group, and Ring B is (a) a benzene ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; (b) an unsaturated monocyclic heterocyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mono- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group;

(2) Ring A is a benzene ring which may optionally be substituted by a halogen atom, a lower alkyl group, a halo-lower alkyl group, a lower alkoxy group, a phenyl group, or a lower alkenylene group, and Ring B is (a) an unsaturated monocyclic heterocyclic ring which may optionally be substituted by a halogen atom; a cyano group; a lower alkyl group; a halo-lower alkyl group; a phenyl-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, a mono- or di-lower alkylamino group, or a carbamoyl group; or a heterocyclyl group optionally substituted by a halogen atom, a cyano group, a lower alkyl group, a halo-lower alkyl group, a lower alkoxy group, a mono- or di-lower alkylamino group or a carbamoyl group; (b) an unsaturated fused heterobicyclic ring which may optionally be substituted by a group selected from a halogen atom, cyano group, a lower alkyl group, a halo-lower alkyl group, a phenyl-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (3) Ring A is an unsaturated fused heterobicyclic ring which may optionally be substituted by a halogen atom, a lower alkyl group, a halo-lower alkyl group, a lower alkoxy group, or an oxo group, and Ring B is (a) a benzene ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; (b) an unsaturated monocyclic heterocyclic ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group.

In another preferred embodiment, in the compound of formula (I), Y is —$CH_2$— and is linked at the 3-position of Ring A, with respect to X being the 1-position, Ring A is a benzene ring which is substituted by 1-3 substituents selected from the group consisting of a lower alkyl group, a halo-lower alkyl group, a halogen atom, a lower alkoxy group, a phenyl group, and a lower alkenylene group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a phenyl-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxy phenyl group, a lower alkylenedioxyphenyl group, a lower alkyleneoxy phenyl group, a mono- or di-lower alkylaminophenyl group, a carbamoyl phenyl group, a mono- or di-lower alkylcarbamoylphenyl group, a heterocyclyl group, a haloheterocyclyl group, a cyanoheterocyclyl group, a lower alkylheterocyclyl group, a lower alkoxyheterocyclyl group, a mono- or di-lower alkylaminoheterocycyclyl group, a carbamoylheterocyclyl group, and a mono- or di-lower alkylcarbamoyl group.

In another more preferable embodiment, in the compound of formula (I), Y is —$CH_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is a benzene ring which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a heterocyclyl group, a haloheterocyclyl group, a cyanoheterocyclyl group, a lower alkylheterocyclyl group, and a lower alkoxyheterocyclyl group.

Further, in another preferable embodiment, in the compound of formula (I), Y is —$CH_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxyphenyl group, a heterocyclyl group, a haloheterocyclyl group, a cyanoheterocyclyl group, a lower alkylheterocyclyl group, and a lower alkoxyheterocyclyl group. In a more preferable embodiment of the present invention, X is a carbon atom and Y is —$CH_2$—.

Further, in another preferable embodiment, in the compound of formula (I), Ring A and Ring B are (1) Ring A is a benzene ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, a phenyl group, and a lower alkenylene group, and Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group, a halo-lower alkoxy group, or a carbamoyl group; a heterocyclyl group optionally substituted by a halogen atom, a cyano group, a lower alkyl group, a halo-lower alkyl group, a lower alkoxy group, a halo-lower alkoxy group or a carbamoyl roup; and an oxo group, (2) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, and Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; a lower alkylene group, (3) Ring A is an unsaturated monocyclic heterocyclic ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group;

(4) Ring A is an unsaturated fused heterobicyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and a lower alkylene group, or (5) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group.

In another preferable embodiment, in the compound of formula (I), Y is linked at the 3-position of Ring A, with respect to X being the 1-position, Ring A is a benzene ring which may optionally be substituted by a halogen atom, a lower alkyl group optionally substituted by a halogen atom, a lower alkoxy group, or a phenyl group, and Ring B is an unsaturated monocyclic heterocyclic ring or an unsaturated fused heterobicyclic ring which may optionally be substituted by 1-3 substituents, independently selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and an oxo group.

In another more preferable embodiment, in the compound of formula (I), Y is linked at the 3-position of Ring A, with respect to X being the 1-position, Ring A is an unsaturated monocyclic heterocyclic ring which may optionally be substituted by a substituent selected from a halogen atom, a lower alkyl group, and an oxo group, and Ring B is a benzene ring which may optionally be substituted by a substituent selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and a lower alkylene group.

Preferable examples of unsaturated monocyclic heterocyclic ring include a 5- or 6-membered unsaturated heterocyclic ring containing 1 or 2 hetero atoms independently selected from a nitrogen atom, an oxygen atom, and a sulfur atom. More specifically, preferred are furan, thiophene, oxazole, isoxazole, triazole, tetrazole, pyrazole, pyridine, pyrimidine, pyrazine, dihydroisoxazole, dihydropyridine, and thiazole. Preferable unsaturated fused heterobicyclic ring includes a 9- or 10-membered unsaturated fused heterocyclic ring containing 1 to 4 heteroatoms independently selected from a nitrogen atom, an oxygen atom, and a sulfur atom. More specifically, preferred are indoline, isoindoline, benzothiazole, benzoxazole, indole, indazole, quinoline, isoquinoline, benzothiophene, benzofuran, thienothiophene, and dihydroisoquinoline.

In a more preferred embodiment, in the compound of formula (I), Ring A is a benzene ring which may optionally be substituted by a substituent selected from the group consisting of a halogen atom, a lower alkyl group, a halo-lower alkyl group, a lower alkoxy group, and a phenyl group, and Ring B is a heterocyclic ring selected from the group consisting of thiophene, furan, benzofuran, benzothiophene, and benzothiazole, wherein the heterocyclic ring may optionally be substituted by a substituent selected from the following group: a halogen atom, a cyano group, a lower alkyl group, a halo-lower alkyl group, a phenyl-lower alkyl group, a lower alkoxy group, a halo-lower alkoxy group, a phenyl group, a halophenyl group, a lower alkylphenyl group, a lower alkoxyphenyl group, a thienyl group, a halothienyl group, a pyridyl group, a halopyridyl group, and a thiazolyl group.

In yet another preferred embodiment, in the compound of formula (I), Y is —CH$_2$—, Ring A is an unsaturated monocyclic heterocyclic ring or an unsaturated fused heterobicyclic ring selected from the group consisting of thiophene, dihydroisoquinoline, dihydroisoxazole, triazole, pyrazole, dihydropyridine, dihydroindole, indole, indazole, pyridine, pyrimidine, pyrazine, quinoline, and a isoindoline, wherein the heterocyclic ring may optionally substituted by a substituent selected from the following group: a halogen atom, a lower alkyl group, and an oxo group, and Ring B is a benzene ring which may optionally be substituted by a substituent selected from the following group: a halogen atom, a lower alkyl group, a halo-lower alkyl group, a lower alkoxy group, and a halo-lower alkoxy group.

In a further preferred embodiment, in the compound of formula (I), Ring A is a benzene ring which is substituted by a halogen atom or a lower alkyl group, and Ring B is thienyl group which is substituted by phenyl group or a heterocyclyl group in which said phenyl group and heterocyclyl group is substituted by 1-3 substituents selected from a halogen atom, a cyano group, a lower alkyl group, a halo-lower alkyl group, a lower alkoxy group, and a halo-lower alkoxy group.

Further, in another aspect of the present invention, preferable examples of the compound of the formula (I) include a compound wherein Ring A is

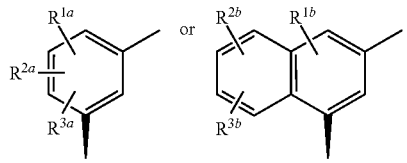

wherein $R^{1a}$, $R^{2a}$, $R^{3a}$, $R^{1b}$, $R^{2b}$, and $R^{3b}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, a phenyl group, a phenylalkoxy group, a cyano group, a nitro group, an amino group, a mono- or di-alkylamino group, an alkanoylamino group, a carboxyl group, an alkoxycarbonyl group, a carbamoyl group, a mono- or di-alkylcarbamoyl group, an alkanoyl group, an alkylsulfonylamino group, a phenylsulfonylamino group, an alkylsulfinyl group, an alkylsulfonyl group, or a phenylsulfonyl group, and Ring B is

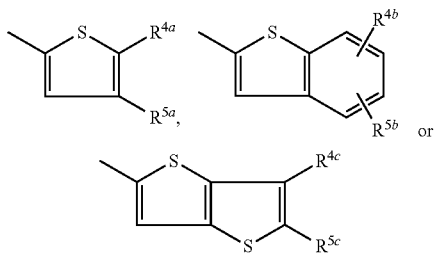

wherein $R^{4a}$ and $R^{5a}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, an alkylenedioxy group, an alkyleneoxy group, a mono- or di-alkylamino group, a carbamoyl group, or a mono- or di-alkylcarbamoyl group; or a heterocyclyl group optionally substituted by a halogen atom, a cyano group, an alkyl group, a haloalkyl group, an alkoxy group, a haloalkoxy group, a carbamoyl group, or a mono- or di-alkylcarbamoyl group, or $R^{4a}$ and $R^{5a}$ are bonded to each other at the terminals thereof to form an alkylene group; and $R^{4b}$, $R^{5b}$, $R^{4c}$ and $R^{5c}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, a methylenedioxy group, an ethyleneoxy group, or a mono- or di-alkylamino group; or a heterocyclyl group optionally substituted by a halogen atom, a cyano group, an alkyl group, a haloalkyl group, an alkoxy group or a haloalkoxy group.

More preferred is a compound of formula (I) wherein $R^{1a}$, $R^{2a}$, $R^{3a}$, $R^{1b}$, $R^{2b}$, and $R^{3b}$ are each independently a hydrogen atom, a halogen atom, a lower alkyl group, a halo-lower alkyl group, a lower alkoxy group, or a phenyl group;

$R^{4a}$ and $R^{5a}$ are each independently a hydrogen atom; a halogen atom; a lower alkyl group; a halo-lower alkyl group; a phenyl-lower alkyl group; a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, or $R^{4a}$ and $R^{5a}$ are bonded to each other at the terminals thereof to form a lower alkylene group; and $R^{4b}$, $R^{5b}$, $R^{4c}$ and $R^{5c}$ are each independently a hydrogen atom, a halogen atom, a lower alkyl group, a halo-lower alkyl group, a lower alkoxy group, or a halo-lower alkoxy group.

Further preferred is a compound of formula (I) in which Ring B is a ring of the following structure

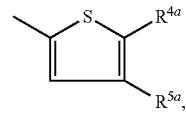

wherein $R^{4a}$ is a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, or $R^{4a}$ and $R^{5a}$ are bonded to each other at the terminals thereof to form a lower alkylene group.

Further more preferred, is a compound of formula (I) in which Ring A is

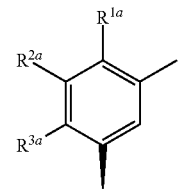

wherein $R^{1a}$ is a halogen atom, a lower alkyl group, or a lower alkoxy group, and $R^{2a}$ and $R^{3a}$ are hydrogen atoms; and Ring B is

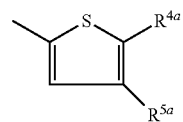

wherein $R^{4a}$ is a phenyl group optionally substituted by a substituent selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, and Y is —CH$_2$—.

In more preferable embodiment, in the compound of formula (I), $R^{4a}$ is a phenyl group optionally substituted by a halogen atom, a cyano group, a lower alkyl group, a halo-lower alkyl group, a lower alkoxy group, or a halo-lower alkoxy group; or a heterocyclyl group optionally substituted by a halogen atom, a cyano group, a lower alkyl group, or a lower alkoxy group.

In another embodiment, a preferable compound of formula (I) can be represented by the following formula (IA):

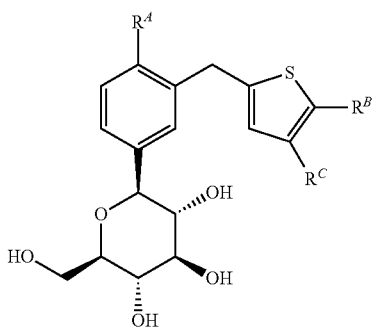

(IA)

wherein $R^A$ is a halogen atom, a lower alkyl group or a lower alkoxy group; $R^B$ is a phenyl group optionally substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group optionally substituted by 1-3 substituents selected from a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; and $R^C$ is hydrogen atom; or $R^B$ and $R^C$ taken together are a fused benzene ring which may be substituted by a halogen atom, a lower alkyl group, a halo-lower alkyl group, a lower alkoxy group or a halo-lower alkoxy group.

In a preferable embodiment, in the compound of formula (I), $R^A$ is a halogen atom or a lower alkyl group, $R^C$ is hydrogen atom, and $R^B$ is phenyl group substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group. The chemical structure of such compounds are represented by the following formula (IA'):

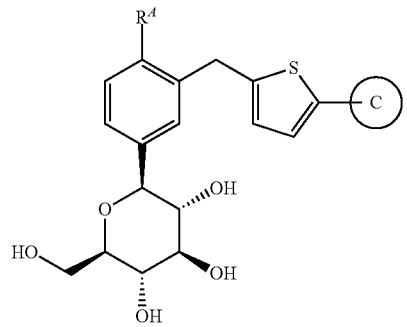

(IA')

wherein $R^A$ is a halogen atom, or a lower alkyl group, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group.

In a more preferable embodiment, in the compound of formula (I), Ring C is a phenyl group substituted by 1-3 substituents selected from the group consisting of a halogen atom, a cyano group, a lower alkyl group, a halo-lower alkyl group, a lower alkoxy group, a halo-lower alkoxy group, and a mono- or di-lower alkylamino group; or a heterocyclyl group substituted by a substituent selected from the group consisting of a halogen atom, a cyano group, a lower alkyl group, a halo-lower alkyl group, a lower alkoxy group, and a halo-lower alkoxy group.

Among them, a compound of formula (I) in which Ring C is a phenyl group substituted by a halogen atom, a cyano group, a lower alkyl group, a halo-lower alkyl group, a lower alkoxy group or a halo-lower alkoxy group; or a heterocyclyl group substituted by a halogen atom, a cyano group, a lower alkyl group, or a lower alkoxy group is preferred.

A preferred heterocyclyl group includes a 5- or 6-membered heterocyclyl group containing 1 or 2 hetero atoms independently selected from the group consisting of a nitrogen atom, an oxygen atom, and a sulfur atom, or a 9- or 10-membered heterocyclyl group containing 1 to 4 hetero atoms independently selected from the group consisting of a nitrogen atom, an oxygen atom, and a sulfur atom. Specifically, a thienyl group, a pyridyl group, a pyrimidyl group, a pyrazinyl group, pyrazolyl group, a thiazolyl group, a quinolyl group, a tetrazolyl group and an oxazolyl group are preferred.

In a further preferable embodiment, in the compound of formula (I), Ring C is a phenyl group substituted by a halogen atom or a cyano group, or a pyridyl group substituted by a halogen atom.

In another embodiment, preferred is a compound of formula (I), in which Ring A is

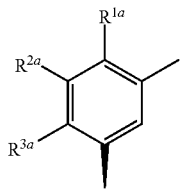

wherein $R^{1a}$ is a halogen atom, a lower alkyl group, or a lower alkoxy group, and $R^{2a}$ and $R^{3a}$ are hydrogen atoms; and Ring B is

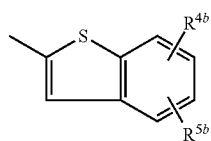

wherein $R^{4b}$ and $R^{5b}$ are each independently a hydrogen atom, a halogen atom, a lower alkyl group, a halo-lower alkyl group, a lower alkoxy group, or a halo-lower alkoxy group.

In another aspect of the present invention, preferable examples of the compound of formula (I), include a compound represented by the following formula (IB):

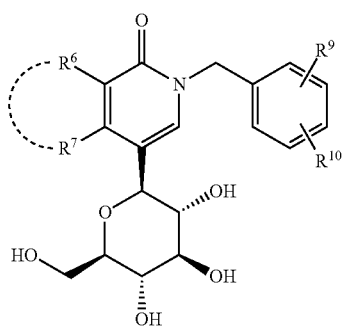

(IB)

wherein $R^8$, $R^9$ and $R^{10}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryloxy group, an arylalkoxy group, a cyano group, a nitro group, an amino group, a mono- or di-alkylamino group, an alkylcarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, or an arylsulfonyl group; and a group represented by:

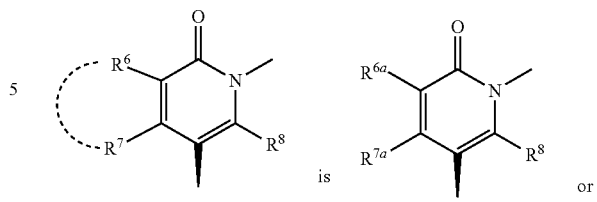

wherein $R^{6a}$ and $R^{7a}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryloxy group, an arylalkoxy group, a cyano group, a nitro group, an amino group, a mono- or di-alkylamino group, an alkylcarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, or an arylsulfonyl group and $R^{6b}$ and $R^{7b}$ are each independently a hydrogen atom, a halogen atom, an alkyl group, a haloalkyl group, or an alkoxy group.

Among the compounds represented by the formula (IB), more preferred is a compound in which $R^8$, $R^9$ and $R^{10}$ are each independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group, and a group represented by:

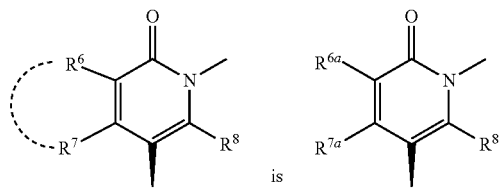

wherein $R^{6a}$, $R^{7a}$ are each independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group, or a group represented by:

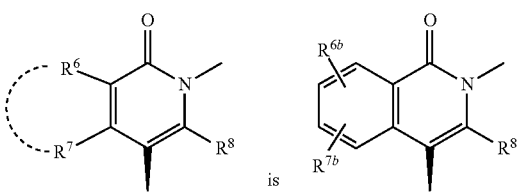

wherein $R^{6b}$ and $R^{7b}$ are each independently a hydrogen atom, a halogen atom, a lower alkyl group, a halo-lower alkyl group, or a lower alkoxy group.

In another aspect, preferable examples of the compound of formula (I) include a compound represented by the following formula (IC):

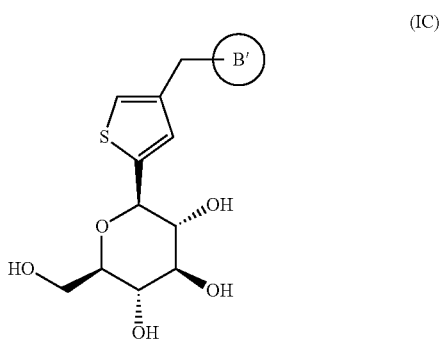

wherein Ring B' is an optionally substituted benzene ring, an optionally substituted unsaturated monocyclic heterocyclic ring, or an optionally substituted unsaturated fused heterobicyclic ring.

Preferable examples of Ring B' include a benzene ring and a heterocyclic ring, both of which may have a substituent(s) selected from the group consisting of a halogen atom; a cyano group; a lower alkyl group optionally substituted by a halogen atom; a lower alkoxy group optionally substituted by a halogen atom; a lower alkanoyl group; a mono- or di-lower alkylamino group; a lower alkoxycarbonyl group; a carbamoyl group; a mono- or di-lower alkylcarbamoyl group; a phenyl group optionally substituted by a substituent(s) selected from a halogen atom, a cyano group, a lower alkyl group optionally substituted by a halogen atom, a lower alkoxy group optionally substituted by a halogen atom, a lower alkanoyl group, a mono- or di-lower alkylamino group, a lower alkoxycarbonyl group, a carbamoyl group, or a mono- or di-lower alkylcarbamoyl group; a heterocyclyl group optionally substituted by a substituent(s) selected from a halogen atom, a cyano group, a lower alkyl group optionally substituted by a halogen atom, a lower alkoxy group optionally substituted by a halogen atom, a lower alkanoyl group, a mono- or di-lower alkylamino group, a lower alkoxycarbonyl group, a carbamoyl group, or a mono- or di-lower alkylcarbamoyl group; an alkylene group; and an oxo group.

More preferable examples of Ring B' include a benzene ring which may be substituted by a substituent selected from the group consisting of a halogen atom; a cyano group; a lower alkyl group optionally substituted by a halogen atom; a lower alkoxy group optionally substituted by a halogen atom; a mono- or di-lower alkylamino group; a phenyl group optionally substituted by a halogen atom, a cyano group, a lower alkyl group optionally substituted by a halogen atom, a lower alkoxy group optionally substituted by a halogen atom; a heterocyclyl group optionally substituted by a halogen atom, a cyano group, a lower alkyl group optionally substituted by a halogen atom, a lower alkoxy group optionally substituted by a halogen atom.

Preferred compound of formula (I) may be selected from the group consisting of:
1-(β-D-glucopyranosyl)-4-chloro-3-(6-ethylbenzo[b]thiophen-2-ylmethyl)benzene;
1-(β-D-glucopyranosyl)-4-chloro-3-[5-(5-thiazolyl)-2-thienylmethyl]benzene;
1-(β-D-glucopyranosyl)-4-chloro-3-(5-phenyl-2-thienylmethyl)benzene;
1-(β-D-glucopyranosyl)-4-methyl-3-[5-(4-fluorophenyl)-2-thienylmethyl]benzene;
1-(β-D-glucopyranosyl)-4-chloro-3-[5-(2-pyrimidinyl)-2-thienylmethyl]benzene;
1-(β-D-glucopyranosyl)-4-methyl-3-[5-(2-pyrimidinyl)-2-thienylmethyl]benzene;
1-(β-D-glucopyranosyl)-4-chloro-3-[5-(3-cyanophenyl)-2-thienylmethyl]benzene;
1-(β-D-glucopyranosyl)-4-chloro-3-[5-(4-cyanophenyl)-2-thienylmethyl]benzene;
1-(β-D-glucopyranosyl)-4-methyl-3-[5-(6-fluoro-2-pyridyl)-2-thienylmethyl]benzene;
1-(β-D-glucopyranosyl)-4-chloro-3-[5-(6-fluoro-2-pyridyl)-2-thienylmethyl]benzene;
1-(β-D-glucopyranosyl)-4-methyl-3-[5-(3-difluoromethylphenyl)-2-thienylmethyl]benzene;
1-(β-D-glucopyranosyl)-4-methyl-3-[5-(3-cyanophenyl)-2-thienylmethyl]benzene;
1-(β-D-glucopyranosyl)-4-methyl-3-[5-(4-cyanophenyl)-2-thienylmethyl]benzene;
1-(β-D-glucopyranosyl)-4-chloro-3-[5-(6-fluoro-3-pyridyl)-2-thienylmethyl]benzene;
1-(β-D-glucopyranosyl)-4-fluoro-3-(5-(3-cyanophenyl)-2-thienylmethyl)benzene;
a pharmaceutically acceptable salt thereof; and a prodrug thereof.

Particularly preferred compounds of formula (I) include:
1-(β-D-glucopyranosyl)-4-methyl-3-[5-(3-cyano-phenyl)-2-thienylmethyl]benzene, or a pharmaceutically acceptable salt thereof, or a prodrug thereof;
1-(β-D-glucopyranosyl)-4-methyl-3-[5-(4-cyano-phenyl)-2-thienylmethyl]benzene, or a pharmaceutically acceptable salt thereof, or a prodrug thereof;
1-(β-D-glucopyranosyl)-4-methyl-3-[5-(4-fluoro-phenyl)-2-thienylmethyl]benzene, or a pharmaceutically acceptable salt thereof, or a prodrug thereof;
1-(β-D-glucopyranosyl)-4-chloro-3-[5-(3-cyano-phenyl)-2-thienylmethyl]benzene, or a pharmaceutically acceptable salt thereof, or a prodrug thereof;
1-(β-D-glucopyranosyl)-4-methyl-3-[5-(6-fluoro-2-pyridyl)-2-thienylmethyl]benzene, or a pharmaceutically acceptable salt thereof, or a prodrug thereof;
1-(β-D-glucopyranosyl)-4-chloro-3-[5-(6-fluoro-2-pyridyl)-2-thienylmethyl]benzene, or a pharmaceutically acceptable salt thereof, or a prodrug thereof;
1-(β-D-glucopyranosyl)-4-chloro-3-[5-(6-fluoro-3-pyridyl)-2-thienylmethyl]benzene, or a pharmaceutically acceptable salt thereof, or a prodrug thereof; and
1-(β-D-glucopyranosyl)-4-fluoro-3-(5-(3-cyanophenyl)-2-thienylmethyl)benzene, or a pharmaceutically acceptable salt thereof, or a prodrug thereof.

The pharmaceutically acceptable salt of the compounds of the formula (I) includes, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octylamine, tris(hydroxymethyl)aminomethane, N-methyl glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The term "prodrug" means an ester or carbonate, which is formed by reacting one or more hydroxy groups of the compound of the formula (I) with an acylating agent substituted by an alkyl, an alkoxy or an aryl by a conventional method to produce acetate, pivalate, methylcarbonate, benzoate, etc. Further, the prodrug includes also an ester or amide, which is similarly formed by reacting one or more hydroxy groups of the compound of the formula (I) with an α-amino acid or a β-amino acid, etc. using a condensing agent by a conventional method.

The compounds of formula (I) also includes a mixture of stereoisomers, or each pure or substantially pure isomer. For example, the present compound may optionally have one or more asymmetric centers at a carbon atom containing any one of substituents. Therefore, the compounds of the formula (I) may exist in the form of enantiomer or diastereomer, or a mixture thereof. When the compounds of formula (I) contains a double bond, the present compound may exist in the form of geometric isomerism (cis-compound, trans-compound), and when the compounds of formula (I) contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization.

In addition, the compounds of formula (I) include an intramolecular salt, hydrate, solvate or polymorphism thereof.

The methods of the present inventions are directed to the treatment and or prevention (including delay in the progression or onset of) of "glucose-related disorders". As used herein, the term "glucose related disorder" shall be defined as any disorder which is characterized by or is developed as a consequence of elevated glucose levels. Glucose-related disorders shall include diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glucose, hyperlipidemia, obesity, hypertriglyceridemia, Syndrome X, diabetic complications, atherosclerosis, or hypertension. In particular, the "glucose related-disorder" is diabetes mellitus (type 1 and type 2 diabetes mellitus, etc.), diabetic complications (such as diabetic retinopathy, diabetic neuropathy, diabetic nephropathy), obesity, or postprandial hyperglycemia.

In an embodiment of the present invention, the glucose related disorder is selected from the group consisting of diabetes mellitus, diabetic retinopathy, diabetic neuropathy, diabetic nephropathy, delayed wound healing, insulin resistance, hyperglycemia, hyperinsulinemia, elevated blood levels of fatty acids, hyperlipidemia, obesity, hypertriglyceridemia, Syndrome X, diabetic complications, atherosclerosis and hypertension.

In another embodiment of the present invention, the glucose related disorder is selected from the group consisting of type 1 diabetes mellitus, type 2 diabetes mellitus, diabetic retinopathy, diabetic neuropathy, diabetic nephropathy, obesity and postprandial hyperglycemia. In another embodiment of the present invention, the glucose related disorder is selected from the group consisting of type 1 diabetes mellitus, type 2 diabetes mellitus, diabetic retinopathy, diabetic neuropathy, diabetic nephropathy, obesity, and delayed wound healing. In another embodiment of the present invention, the glucose related disorders is selected from the group consisting of poor glycemic control, Type 2 Diabetes Mellitus, Syndrome X, gestational diabetes, insulin resistance, hyperglycemia. In another embodiment of the present invention, the glucose related disorder is Type 2 diabetes mellitus.

In another embodiment, the glucose related disorder is selected from the group consisting of elevated glucose level, pre-diabetes, impaired oral glucose tolerance, poor glycemic control, Type 2 Diabetes Mellitus, Syndrome X (also known as metabolic syndrome), gestational diabetes, insulin resistance, and hyperglycemia.

Treatment of glucose related disorders may comprise lowering glucose levels, improving glycemic control, decreasing insulin resistance and/or preventing the development of a glucose related disorder (for example preventing a patient suffering from impaired oral glucose tolerance or elevated glucose levels from developing Type 2 diabetes mellitus).

As used herein, the terms "Syndrome X", "Metabolic Syndrome" and "Metabolic Syndrome X" shall mean a disorder that presents risk factors for the development of Type 2 diabetes mellitus and cardiovascular disease and is characterized by insulin resistance and hyperinsulinemia and may be accompanied by one or more of the following: (a) glucose intolerance, (b) Type 2 diabetes, (c) dyslipidemia, (d) hypertension and (e) obesity.

The term "subject" as used herein, refers to an animal, preferably a mammal, most preferably a human, who has been the object of treatment, observation or experiment.

As used herein, the term "composition" is intended to encompass a product comprising the specified ingredients in the specified amounts, as well as any product which results, directly or indirectly, from combinations of the specified ingredients in the specified amounts.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to co-therapy or combination therapy, comprising administration of (a) metformin or a pharmaceutically acceptable salt thereof and (b) a compound of formula (I) or a pharmaceutically acceptable salt thereof, "therapeutically effective amount" shall mean that amount of the combination of agents taken together so that the combined effect elicits the desired biological or medicinal response. For example, the therapeutically effective amount of co-therapy comprising administration of (a) metformin or a pharmaceutically acceptable salt thereof and (b) a compound of formula (I) or a pharmaceutically acceptable salt thereof, would be the amount of (a) the metformin or a pharmaceutically acceptable salt thereof and (b) the compound of formula (I) or pharmaceutically acceptable salt thereof that when taken together or sequentially have a combined effect that is therapeutically effective. Further, it will be recognized by one skilled in the art that in the case of co-therapy with a therapeutically effective amount, as in the example above, the amount of the (a) metformin or pharmaceutically acceptable salt thereof and/or the amount of the (b) compound of formula (I) or pharmaceutically acceptable salt thereof individually may or may not be therapeutically effective.

One skilled in the art will further recognize that the term "therapeutically effective amount" of co-therapy comprising administration of (a) glyburide, and (b) a compound of formula (I) or a pharmaceutically acceptable salt thereof shall mean that amount of the glyburide and the amount of the compound of formula (I) or pharmaceutically acceptable salt thereof, that when taken together or sequentially have a combined effect that is therapeutically effective; and further that the amount of each of said components individually may or may not be therapeutically effective.

One skilled in the art will further recognize that the "therapeutically effective amount" of co-therapy comprising administration of (a) metformin or a pharmaceutically acceptable salt thereof, (b) a compound of formula (I) or a pharmaceutically acceptable salt thereof and (c) a sulfonylurea (preferably glyburide) or pharmaceutically acceptable salt thereof shall mean that amount of each of the components that when taken together or sequentially have a combined effect that is therapeutically effective; and further that the amount of each of the components individually may or may not be therapeutically effective.

As used herein, the terms "co-therapy" and "combination therapy" shall mean treatment of a subject in need thereof by administering (a) metformin or a pharmaceutically acceptable salt thereof (b) a compound of formula (I) or pharmaceutically acceptable salt thereof and optionally (c) a sulfonylurea (preferably glyburide) or pharmaceutically acceptable salt thereof, wherein the (a) metformin or a pharmaceutically acceptable salt thereof, the (b) compound of formula (I) or pharmaceutically acceptable salt thereof and optionally (c) the sulfonylurea (preferably glyburide) or pharmaceutically acceptable salt thereof are administered by any suitable means, simultaneously, sequentially, separately or in a single pharmaceutical dosage form. Where the (a) metformin or a pharmaceutically acceptable salt thereof, the (b) compound of formula (I) or pharmaceutically acceptable salt thereof and optionally (c) the sulfonylurea (preferably glyburide) or pharmaceutically acceptable salt thereof are administered in separate dosage forms, the number of dosages administered per day for each compound may be the same or different. The (a) metformin or a pharmaceutically acceptable salt thereof, the (b) compound of formula (I) or pharmaceutically acceptable salt thereof and optionally (c) the sulfonylurea (preferably glyburide) or pharmaceutically acceptable salt thereof, may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The (a) metformin or a pharmaceutically acceptable salt thereof, the (b) compound of formula (I) or pharmaceutically acceptable salt thereof and optionally (c) the sulfonylurea (preferably glyburide) or pharmaceutically acceptable salt there may be administered according to simultaneous or alternating regimens, at the same or different times during the course of the therapy, concurrently in divided or single forms. One skilled in the art will further recognize that the above discussion related to "co-therapy" and "combination therapy" will similarly apply to co-therapy or combination therapy for the treatment of a glucose related disorder comprising administration to a subject in need thereof of (a) glyburide, and (b) a compound of formula (I) or pharmaceutically acceptable salt thereof.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The present invention further comprises pharmaceutical compositions containing (a) metformin or a pharmaceutically acceptable salt thereof and (b) a compound of formula (I) or pharmaceutically acceptable salt thereof with a pharmaceutically acceptable excipient. Pharmaceutical compositions of the present invention described herein as the active ingredient can be prepared by intimately mixing the (a) metformin or a pharmaceutically acceptable salt thereof and the (b) compound of formula (I) or pharmaceutically acceptable salt thereof with a pharmaceutical excipient according to conventional pharmaceutical compounding techniques.

The present invention further comprises pharmaceutical compositions containing (a) glyburide, and (b) a compound of formula (I) or pharmaceutically acceptable salt thereof with a pharmaceutically acceptable excipient. Pharmaceutical compositions of the present invention described herein as the active ingredient can be prepared by intimately mixing the (a) glyburide, and the (b) compound of formula (I) or pharmaceutically acceptable salt thereof with a pharmaceutical excipient according to conventional pharmaceutical compounding techniques.

The present invention further comprises pharmaceutical compositions containing (a) metformin or a pharmaceutically acceptable salt thereof, (b) a compound of formula (I) or pharmaceutically acceptable salt thereof, (c) a sulfonylurea or pharmaceutically acceptable salt thereof with a pharmaceutically acceptable excipient. Pharmaceutical compositions of the present invention described herein as the active ingredient can be prepared by intimately mixing the (a) metformin or a pharmaceutically acceptable salt thereof, the (b) compound of formula (I) or pharmaceutically acceptable salt thereof and the (c) sulfonylurea or pharmaceutically acceptable salt thereof with a pharmaceutical excipient according to conventional pharmaceutical compounding techniques.

The pharmaceutically acceptable excipient may take a wide variety of forms depending upon the desired route of administration (e.g., oral, parenteral). Thus for liquid oral preparations such as suspensions, elixirs and solutions, suitable excipients and additives include water, glycols, oils, alcohols, flavoring agents, preservatives, stabilizers, coloring agents and the like; for solid oral preparations, such as powders, capsules and tablets, suitable excipients and additives include diluents, granulating agents, lubricants, binders, disintegrating agents, drug release controlling hydrophilic polymer, drug release controlling hydrophobic polymers, wetting agents and the like. Solid oral preparations may also be coated with substances such as sugars, cellulosic ethers, and acrylic polymers for extended release or may be enteric-coated so as to modulate major site of absorption. For parenteral administration, the excipient will usually consist of sterile water and other ingredients may be added to increase solubility or preservation. Injectable suspensions or solutions may also be prepared utilizing aqueous excipients along with appropriate additives.

To prepare the pharmaceutical compositions of this invention, the compound of formula (I) or pharmaceutically acceptable salt thereof and the (a) metformin or a pharmaceutically acceptable salt thereof and/or the (b) sulfonylurea (preferably glyburide) or pharmaceutically acceptable salt thereof, as the active ingredients, are intimately admixed with a pharmaceutical excipient according to conventional pharmaceutical compounding techniques, which excipient may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable excipients and additives include water, glycols, oils, alcohols, flavoring agents, preservatives, coloring agents and the like; for solid oral preparations such as, for example, powders, capsules, and tablets (including caplets), suitable excipients and additives include diluents, granulating agents, lubricants, binders, disintegrating agents, drug release controlling hydrophilic polymers, drug release controlling or hydrophobic polymers, wetting agents, and the like. Because of their ease in administration, tablets and capsules represent the most advantageous oral dosage unit form, in which case solid pharmaceutical excipients are obviously employed. If desired, tablets may be sugar coated or may be enteric coated by standard techniques. For parenterals, the excipient will usually comprise sterile water, through other ingredients, for example, for purposes such as aiding solubility or for preservation, may be included. Injectable suspensions may also be prepared, in which case appropriate liquid excipients, suspending agents and the like may be employed. The pharmaceutical compositions described herein will contain, per dosage unit, e.g., tablet, capsule, powder, injection, teaspoonful and the like, an amount of the active ingredient(s) necessary to deliver an effective dose as described above. The pharmaceutical compositions herein will contain, per unit dosage unit, e.g., tablet, capsule, powder, injection, suppository, teaspoonful and the like, of from about 0.01 to about 2,000 mg, or any amount or range therein, independently, of each of the (a) metformin or a pharmaceutically acceptable salt thereof, the (b) compound of formula (I) or pharmaceutically acceptable salt thereof, and/or the (c) sulfonylurea (preferably glyburide) or pharmaceutically acceptable salt thereof. The pharmaceutical compositions described herein may be given at a suitably selected therapeutically effective dosage, which may be varied depending upon the requirement of the patients, the severity of the condition being treated and the compound being employed. The use of either daily administration or post-periodic dosing may be employed.

Preferably these pharmaceutical compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the pharmaceutical composition may be presented in a form suitable for once-weekly or once-monthly administration; for example, an insoluble salt of the active compound(s), such as the decanoate salt, may be adapted to provide a depot preparation for intramuscular injection.

For preparing solid compositions such as tablets, the principal active ingredient(s) are mixed with a pharmaceutical excipient, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid formulation composition containing a mixture of the active ingredient(s). The tablets or pills of the pharmaceutical composition of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the pharmaceutical compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Advantageously, the pharmaceutical compositions of the present invention may be administered in a single daily dose, or the total daily dosage may be administered in divided doses of two, three or four times daily. Furthermore, the pharmaceutical compositions of the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

In certain embodiments, for oral administration in the form of a tablet or capsule, the active drug component(s) can be combined with an oral, non-toxic pharmaceutically acceptable inert excipient such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride, and the like. Disintegrators include, without limitation, starch, sodium starch glycolate, croscamellose sodium, crospovidone, methyl cellulose, agar, bentonite, xanthan gum, and the like. The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The pharmaceutical compositions of the present invention may be prepared according to known methods and employing known processes and equipment, as disclosed, for example in *Pharmaceutical Sciences*, Remington, 17th Ed., pp. 1585-1594 (1985); *Chemical Engineers Handbook*, Perry, 6th Ed., pp. 21-13 to 21-19 (1984); *Journal of Pharmaceutical Sciences*, Parrot, Vol. 61, No. 6, pp. 813-829 (1974); and *Chemical Engineer*, Hixon, pp. 94-103 (1990).

Granules for the pharmaceutical compositions of the present invention may, for example, be prepared by comminution, which produces the desired size of the active ingredient and the desired size of any accompanying pharmaceutically acceptable excipient(s). Suitable means for producing the desired particles include, but are not limited to, granulation, spray drying, sieving, lyophilization, crushing, grinding, jet milling, micronizing and chopping to produce the intended particle size. The process can be performed by size reduction equipment, such as a micropulverizer mill, a fluid energy-grinding mill, a grinding mill, a roller mill, a hammer mill, an attrition mill, a chaser mill, a ball mill, a vibrating ball mill, an impact pulverizer mill, a centrifugal pulverizer, a coarse crusher and a fine crusher.

The size of the particle can be ascertained by screening, including a grizzly screen, a flat screen, a vibrating screen, a revolving screen, a shaking screen, an oscillating screen and a reciprocating screen. The granules are then, for example, pressed according to known methods to yield a tablet.

Granules for the pharmaceutical compositions of the present invention may alternatively be manufactured according to the wet granulation technique. In the wet granulation technique, solid particles are wetted and bound together by a binder solution consisting essentially of a granulation solvent, a binder, and optionally other excipients. The active ingredient (for example, the compound of formula (I-X) or pharmaceutically acceptable salt thereof) may be granulated as solid particles together with or absent other solid excipients, or is partially dissolved in the binder solution. The solid particles can be mixed by means of mechanical agitation (using for example, a low or high shear mixer) or may be fluidized by a gas (as in fluid bed granulation). The granulating fluid is added until a wet blend is produced, which wet mass blend is then forced through a predetermined screen and dried in a fluid bed dryer. The blend is dried for about 18 to about 24 hours at a temperature in the range of from about 24° C. to about 35° C. in a forced-air oven. The dried granules are then sized, according to known methods. The dried granules are then sized. Next, magnesium stearate, or another suitable lubricant (if desired) and other excipient materials (as appropriate) are added to the granulation, and the granulation is put into milling jar sand mixed on a jar mill for 10 minutes. For the preparation of tablets, the resulting composition is pressed into a layer, for example, in a Manesty® press or a Korsch LCT press. In an example, the speed of the press is set at 15 rpm and the maximum load set at about 4 tons.

Alternatively, the active ingredient and excipient(s) may be blended as powdered ingredients in a fluid bed granulator. After the powdered ingredients are dry blended in the granulator, a granulating fluid, for example, polyvinylpyrrolidone in water, is sprayed onto the powders. The resulting agglomerated materials are then dried in the granulator. This process granulates all the ingredients present therein while adding the granulating fluid. After the granules are dried, a lubricant, such as stearic acid or magnesium stearate, is mixed into the granulation using a blender e.g., V-blender or tote blender. The granules are then pressed and coated in the manner described above.

Exemplary solvents suitable for manufacturing the pharmaceutical composition components comprise aqueous or inert organic solvents that do not adversely harm the materials used in the system. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethylacetate, isopropyl acetate, n-butyl acetate, methyl isobutyl ketone, methyl propyl ketone, nhexane, n-heptane, ethylene glycol monoethyl ether, ethylene glycol monoethyl acetate, methylene dichloride, ethylene dichloride, propylene dichloride, carbon tetrachloridenitroethane, nitropropane tetrachloroethane, ethyl ether, isopropyl ether, cyclohexane, cyclooctane, benzene, toluene, naphtha, 1,4-dioxane, tetrahydrofuran, diglyme, water, aqueous solvents containing inorganic salts such as sodium chloride, calcium chloride, and the like, and mixtures thereof such as acetone and water, acetone and methanol, acetone and ethyl alcohol, methylene dichloride and methanol, and ethylene dichloride and methanol.

Where desired, pan coating may be used to provide a completed dosage form. In the pan coating system, the coating composition is deposited by successive spraying onto the compressed tablet, accompanied by tumbling in a rotating pan. A pan coater is commonly used because of its availability at commercial scale. Other techniques can be used for coating the tablet. Once coated, the tablet is dried in, for example, the same equipment of in a forced-air oven or in a temperature and humidity controlled oven to free the dosage form of solvent(s) used in the manufacturing. Drying conditions are conventionally chosen on the basis of available equipment, ambient conditions, solvents, coatings, coating thickness, and the like.

Other coating techniques can also be employed. For example, one alternative technique uses an air-suspension procedure. This procedure consists of suspending and tumbling the tablet in a current of air, until a coating is applied. The air-suspension procedure is described in, for example, U.S. Pat. No. 2,799,241; in J. Am. Pharm. Assoc., Vol. 48, pp. 451-459 (1959); and, ibid., Vol. 49, pp. 82-84 (1960). The tablet also can be coated with a Wurster® air-suspension coater using, for example, methylene dichloride methanol as a co-solvent for the coating material. An Aeromatic® air-suspension coater can be used employing a co-solvent.

The co-therapy comprising (a) metformin or a pharmaceutically acceptable salt thereof and (b) a compound of formula (I) or pharmaceutically acceptable salt thereof, of the present invention may be administered in any of the foregoing compositions and according to dosage regimens established in the art whenever treatment of a glucose related disorder is required.

The co-therapy comprising (a) glyburide, and (b) a compound of formula (I) or pharmaceutically acceptable salt thereof, of the present invention may be administered in any of the foregoing compositions and according to dosage regimens established in the art whenever treatment of a glucose related disorder is required.

The co-therapy comprising (a) metformin or a pharmaceutically acceptable salt thereof, (b) a compound of formula (I) or pharmaceutically acceptable salt thereof, and (c) a sulfonylurea (preferably glyburide) or pharmaceutically acceptable salt thereof, of the present invention may be administered in any of the foregoing compositions and according to dosage regimens established in the art whenever treatment of a glucose related disorder is required.

In an embodiment, for oral administration, the compositions are preferably provided in the form of tablets containing, 50, 100, 150, 200, 250, 500, 750, 850, 1000, 1500 or 2000 milligrams of the metformin or pharmaceutically acceptable salt thereof (preferably metformin hydrochloride); and further containing 1, 5, 10, 25, 50, 100, 150, 200, 250, 300 or 500 milligrams of the compound of formula (I) or pharmaceutically acceptable salt thereof. In another embodiment, for oral administration, the compositions are preferably provided in the form of tablets containing, 1.0, 2.5, 5.0, 7.5, 10.0, 12.5, 15 or 20 milligrams, of the glyburide; and further containing 1, 5, 10, 25, 50, 100, 150, 200, 250, 300 or 500 milligrams of the compound of formula (I) or pharmaceutically acceptable salt thereof. In another embodiment, for oral administration, the compositions are preferably provided in the form of tablets containing, 50, 100, 150, 200, 250, 500, 750, 850, 1000, 1500 or 2000 milligrams of the metformin or pharmaceutically acceptable salt thereof (preferably metformin hydrochloride); further containing 1, 5, 10, 25, 50, 100, 150, 200, 250, 300 or 500 milligrams of the compound of formula (I) or pharmaceutically acceptable salt thereof (preferably a compound of formula (I-X) or pharmaceutically acceptable salt thereof or a compound of formula (I-Y) or pharmaceutically acceptable salt thereof), and further containing 1.0, 2.5, 5.0, 7.5, 10.0, 12.5, 15, 20, 25, 50, 100, 250, 500 or 1000 milligrams, of the sulfonylurea or pharmaceutically acceptable salt thereof.

Preferably, the metformin or pharmaceutically acceptable salt thereof (more preferably, metformin hydrochloride) is administered at a dosage level of from about 0.01 mg/kg to about 200 mg/kg of body weight per day, or from about 0.5 mg/kg to about 50 mg/kg of body weight per day, or any amount or range therein. Preferably, the range is from about 1.0 to about 50.0 mg/kg of body weight per day, or any amount or range therein, more preferably, from about 5 mg/kg to about 30 mg/kg, or any amount or range therein, more preferably, from about 5 to about 20 mg/kg of body weight per day, or any amount or range therein. In an embodiment, an effective amount of the metformin or pharmaceutically acceptable salt thereof is supplied at a dosage level of 250 mg, 500 mg, 750 mg, 1000 mg or 2000 mg, or any amount or range therein.

Preferably, the glyburide is administered at a dosage level of from about 0.01 mg/kg to about 0.5 mg/kg of body weight per day, or from about 0.01 mg/kg to about 0.3 mg/kg of body weight per day, or any amount or range therein. In an embodiment, an effective amount of the glyburide is supplied at a dosage level of 1.0 mg, 2.5 mg, 5.0 mg, 7.5 mg, 10.0 mg, 12.5 mg, 15 mg, or 20 mg, or any amount or range therein.

Preferably, the compound of formula (I) or pharmaceutically acceptable salt thereof is administered at a dosage level of from about 0.01 mg/kg to about 500 mg/kg of body weight per day, or 0.01 mg/kg to about 200 mg/kg of body weight per day, or any amount or range therein. Preferably, the range is from about 0.01 to about 50 mg/kg of body weight per day, or any amount or range therein, more preferably, from about 0.05 mg/kg to about 10 mg/kg, or any amount or range therein, more preferably, from about 1 to about 5 mg/kg of body weight per day, or any amount or range therein. In an embodiment, an effective amount of the compound of formula (I) or pharmaceutically acceptable salt thereof is supplied at a dosage level of 10 mg, 25 mg, 50 mg, 100 mg, 150 mg or 300 mg, or any amount or range therein. Preferably, the sulfonylurea or pharmaceutically acceptable salt thereof is administered at a dosage level of from about 0.01 mg/kg to about 200 mg/kg of body weight per day, or any amount or range therein. Preferably, the range is from about 0.01 to about 50 mg/kg of body weight per day. In an embodiment, an effective amount of the sulfonylurea or pharmaceutically acceptable salt thereof is supplied at a dosage level of 1.0 mg, 2.5 mg, 5.0 mg, 10 mg, 25 mg, 50 mg, 100 mg, 150 mg, 250 mg, 500 mg, 100 mg, or any amount or range therein. The co-therapy of the present invention may be administered on a regimen of 1 to 4 times per day.

Optimal dosages to be administered may be readily determined by those skilled in the art, and will vary with for example, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound or co-therapy to treat or prevent a given disorder. One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

An ability and unexpected synergistic effect of co-therapy of metformin and the compound of formula (I) to treat glucose related disorders, for example, Type 2 diabetes mellitus and Syndrome X, is based on the following animal study.

Example 1: In Vivo Mouse Study

Male C57BL/6 mice (total of 100 mice) were fed with a high fat diet from the age of 3 weeks to 6 weeks (total 3 weeks). After 3 weeks on a high fat diet, all the mice received a single-dose ip injection of Steptozotocin (STZ) (100 mg/kg, in 0.05 mol/L citric acid, pH4.5, 10 mg/ml). All the mice were then kept on a high fat diet for another 3 weeks. Those mice with fasted blood glucose levels>7 mM and <15 mM were selected for the study.

At the start of the pre-dose period, each mouse was assigned a predose number, which was indicated on its cage card. After assignment to dosage groups, each mouse was assigned a unique study identification number (which will be indicated on its cage card) and identified by permanent marker on its tail. Mice were housed 5 mice per cage in stainless steel cages. The study room was maintained on a 12-hour light/dark cycle (light/dark cycle may be interrupted for study-related activities), within a temperature range of 64° F. to 79° F., and a relative humidity range of 30% to 70%. The temperature and humidity ranges will be monitored by a hygrothermograph. Mice were fed ad libitum (except where noted) with high-fat diet prepared in Southern University. Water was provided ad libitum by water bottles.

Study Design:

The quarantine period was 5 days. The test compound or vehicle was administered orally by gavage. The dosage levels were chosen to represent a range of exposures with pharmacology effects.

Mice were selected on the basis of pre-dose evaluations at day −1 and randomly assigned to groups using a computer-generated randomization method based on body weight and fasted blood glucose levels. The mean values of body weight and fasted blood glucose level of each group were similar (within <5% variation).

The mice were randomly divided into six testing group of 10 mice per group. Each group was treated for 3 weeks, via oral administration, with one of the following regimens: (a) vehicle; (b) the compound of formula (I-Y) at 1 mg/kg; (c) the compound of formula (I-Y) at 10 mg/kg; (d) metformin at 500 mg/kg; (e) a combination of the compound of formula (I-Y) at 1 mg/kg and metformin at 500 mg/kg; and (f) a combination of the compound of formula (I-Y) at 10 mg/kg and metformin at 500 mg/kg.

On Day 1 (the first day of dosing), dosing at all dose levels was initiated. All groups were then dosed for 20 additional days. The following pharmacological parameters were measured during and at the end of this study: (a) fed blood glucose were measured at day 1, 7, 14, and 21 day before dosing; (b) body weight of each mouse was measured at day −1 (for grouping), 1, 7, 14, and 21, after blood glucose measurement; and (c) 24 hr food intake (average of 5 mice per cage) was measured at day 1, 7, 14, and 20.

On day 18 of treatment, mice were fasted overnight (5 pm-8 am), after a change to a new cage. The following morning, a basal fasted blood glucose level was determined. Then, glucose solution (20% glucose, 2 g/kg body weight, 1 ml/100 g of body weight, prepared freshly before oral glucose tolerance test, (OGTT) was administrated via oral gavage. Blood glucose levels were measured using tail blood at 30, 60, and 120 min after glucose challenge. Food was replaced after the last time point of blood glucose measurement.

The pharmacological significance of any findings was determined based on statistical analysis and historical control data. Statistical analyses were performed utilizing GraphPadPRISM.

The compound of formula (I-Y) alone and in combination with metformin was tested according to the procedure as described above, with results as listed in Table 1, below.

TABLE 1 in vivo Mouse Assay Results

| Treatment | Fed Glucose (mg/dL) | Fasted Glucose (mg/dL) | Blood Glucose AUC during OGTT (mg/dL * 2 h) |
|---|---|---|---|
| Vehicle | 421.5 ± 25.9 | 87.0 ± 6.1 | 36951 ± 2592 |
| Cmpd (I-Y) (1 mg/kg) | 360.7 ± 15.7 | 77.8 ± 4.9 | 31562 ± 1447 |
| Cmpd (I-Y) (10 mg/kg) | 290.5 ± 24.8 | 66.9 ± 3.1 | 25209 ± 894 |
| Metformin (500 mg/kg) | 345.4 ± 28.4 | 74.7 ± 3.8 | 34023 ± 1618 |
| Cmpd (I-Y) (1 mg/kg) + Metformin (500 mg/kg) | 290.0 ± 15.4 | 75.7 ± 11.3 | 28934 ± 1464 |
| Cmpd (I-Y) (10 mg/kg) + Metformin (500 mg/kg) | 223.7 ± 12.2 | 54.1 ± 4.1 | 19395 ± 584 |

| Treatment | Fed Glucose (% relative to the Vehicle) | Fasted Glucose (% relative to the Vehicle) | Blood Glucose AUC during OGTT (% relative to the Vehicle) |
|---|---|---|---|
| Vehicle | 100% ± 6% | 100.0% ± 7.0% | 100% ± 7% |
| Cmpd (I-Y) (1 mg/kg) | 86% ± 4% | 89.4% ± 5.7% | 85% ± 4% |
| Cmpd (I-Y) (10 mg/kg) | 69% ± 6% | 76.9% ± 3.6% | 68% ± 2% |
| Metformin (500 mg/kg) | 82% ± 7% | 85.9% ± 4.4% | 92% ± 4% |
| Cmpd (I-Y) (1 mg/kg) + Metformin (500 mg/kg) | 69% ± 4% | 87.0% ± 13.0% | 78% ± 4% |
| Cmpd (I-Y) (10 mg/kg) + Metformin (500 mg/kg) | 53% ± 3% | 62.2% ± 4.7% | 52% ± 2% |

Example 2: In Vivo Mouse Study

Male ob/ob mice (8-week old, ~50 g) were housed 2 mice per cage in a temperature-controlled room with 12-hour light/dark cycle. The mice were allowed ad libitum access to water and chow (commercially supplied diet). Mice were grouped into 6 test groups based on their body weight and fed blood glucose levels, as noted in Table 2, below.

TABLE 2

Mouse Treatment groups

| Group | Treatment |
|---|---|
| 1 | Vehicle (0.5% Methocel) 1 ml/100 g, P.O. |
| 2 | Compound of formula (I-X) @ 1.0 mpk: 1 ml/100 g, P.O. |
| 3 | Compound of formula (I-X) @ 10.0 mpk: 1 ml/100 g, P.O. |
| 4 | Metformin HCl: 250 mpk: 1 ml/100 g, P.O. |
| 5 | Compound of formula (I-X) @ 1 mpk Metformin HCl: 250 mpk, 1 ml/100 g, P.O. |
| 6 | Compound of formula (I-X) @ 10 mpk Metformin HCl: 250 mpk, 1 ml/100 g, P.O. |

Study Design:

On the first morning, the mice were grouped as noted above and fed glucose. The mice were then dosed with vehicle or test compound(s) via gavage at 4:00 pm each day for 22 days q.d. The compound of formula (I-X) was dosed at 1 mg/kg or 10 mg/kg (as noted in the result table below) with or without treatment with metformin HCl at a dosage of 250 mg/kg.

Body weight, food intake and fed blood glucose levels were measured weekly. An oral glucose tolerance test (OGTT) was conducted on the mice on day 18, after overnight fasting. Glucose concentrations of 0.5 g/kg BW, and blood glucose levels of OGTT were measured using a Glucometer at $t_0$ (before glucose dosing), $t_{30}$, $t_{60}$, and $t_{120}$ corresponding to 30, 60 and 120 minutes following administration. The administered glucose solution was prepared at 0.5 g/kg using 12.5% glucose, 1 ml/250 g BW.

Following completion of the study, final body weight and blood glucose level of were collected and the mice in each group was sacrificed to collect blood for biochemistry analysis, including fed blood glucose levels, fasted blood glucose levels, blood glucose levels during OGTT, plasma insulin and body weight change.

The compound of formula (I-X) alone and in combination with metformin was tested according to the procedure as described above, with results as listed in Table 3, below.

TABLE 3 in vivo ob/ob Mouse Assay Results

| Treatment | Fed Glucose (mg/dL) | Fasted Glucose (mg/dL) | Blood Glucose AUC during OGTT (mg/dL * 2 h) |
|---|---|---|---|
| Vehicle | 345 ± 19 | 174 ± 11 | 100 ± 5 |
| Cmpd (I-X) (1 mg/kg) | 312 ± 34 | 159 ± 12 | 80 ± 4 |
| Cmpd (I-X) (10 mg/kg) | 254 ± 22 | 86 ± 4 | 48 ± 3 |
| Metformin HCl (250 mg/kg) | 371 ± 35 | 166 ± 16 | 91 ± 9 |
| Cmpd (I-X) (1 mg/kg) + Metformin HCl (250 mg/kg) | 285 ± 23 | 153 ± 12 | 77 ± 7 |
| Cmpd (I-X) (10 mg/kg) + Metformin HCl (250 mg/kg) | 216 ± 10 | 110 ± 11 | 56 ± 3 |

| Treatment | Plasma Insulin (ng/dL) | Body Weight (g) |
|---|---|---|
| Vehicle | 38.6 ± 3.3 | 54 ± 0.8 |
| Cmpd (I-X) (1 mg/kg) | 46.3 ± 3.5 | 53 ± 0.8 |
| Cmpd (I-X) (10 mg/kg) | 44.0 ± 3.6 | 54 ± 0.8 |
| Metformin HCl (250 mg/kg) | 48.4 ± 2.0 | 52 ± 0.9 |
| Cmpd (I-X) (1 mg/kg) + Metformin HCl (250 mg/kg) | 52.6 ± 1.2 | 53 ± 0.8 |
| Cmpd (I-X) (10 mg/kg) + Metformin HCl (250 mg/kg) | 53.1 ± 1.4 | 51 ± 1.0 |

The results in Table 3 above indicate that the compound of formula (I-X) at 10 mg/kg significantly reduced blood glucose levels and improved glucose excursion during OGTT. The results further showed no additive or synergistic effect in mice treated with the combination of metformin and the compound of formula (I-X). Additionally, the results show that metformin at 250 mg/kg did not have an effect on blood glucose control, suggesting that the ob/ob mouse is not a suitable animal model to demonstrate the activity of metformin (given the mechanism by which metformin acts on glucose levels). The lack of an additive and/or synergistic effect for the combination of the compound of formula (I-X) and metformin, is therefore believed to be a result of this model's limitation in demonstrating known anti-diabetic activity.

Example 3 Pharmaceutical Composition—Combination of Metformin Hydrochloride and the Compound of Formula (I-X)

A pharmaceutical composition comprising metformin hydrochloride and the compound of formula (I-X) was prepared as follows, with Table 4, below listing the components in the formulation. Metformin HCl was purchased as commercially available Drug Substance (DS) from Solmag S.P.A Mulazzano (Via Della Vittoria 89, 26837 Cassino d' Alberi, Mulazzano, Italy).

TABLE 4

Combination Tablet Formulation

| Description | Function | mg/tablet | % w/w | Quanity/Batch (g) |
|---|---|---|---|---|
| Intragranular Additions | | | | |
| Compound of Formula (I-X) | Drug Substance-1 | 200.0 | 14.69 | 132.2 |
| Metformin HCl | Drug Substance-2 | 1000.0 | 73.46 | 660.8 |
| Microcrystalline Cellulose | Filler | 59.2 | 4.35 | 39.1 |
| Povidone (K29/32)[1] | Binder | 54.50 | 4.00 | 36.0 |
| Croscarmellose sodium | Disintegrant | 40.80 | 3.00 | 27.3 |
| Water[2] | NA | N/A | | |
| Extragranular Additions | | | | |
| Magnesium Stearate, 2257 | Lubricant | 6.8 | 0.50 | 4.5 |
| Totals | | 100.0 | 1361.3 | 100.0 | 899.6 |

[1]Added as 6% solids in solution
[2]Not in final formulation

Metformin hydrochloride, the compound of formula (I-X), microcrystalline cellulose (MCC) and croscarmellose sodium were screened and blended in bohle bin blender (L.B Bohle Maschinen+Verfhren GmbH, Ennigerloh, Germany). The resulting materials were fluidized in a Glatt Fluid bed processor (Glatt Air Techniques, Ramsay, N.J.) with 1.0 mm nozzle and aircap setting of 2. The binder (Povidone K29/32), as a 6% w/w solids solution in water, was then sprayed onto the resulting granules. The moisture level and granulation growth were monitored during the process, with samples taken every 10 minutes of the process. Moisture balance was used to determine loss on drying (LOD).

The dried granulation was then lubricated with screened magnesium stearate in a bohle bin blender. The final blend was compressed into tablets on a rotary press, Fette 1200i (Fette GmbH, Schwarzenbek, Germany) equipped with 0.830"×0.4095" D-tooling and low quantity feeder. The Batch was compressed using two stations to the target tablet weight. Five different compression profiles were used to produce tablets.

For the five compression profile sub-batches, tablet weight variation was less than 1% and friability was less than 0.5%. Tablet hardness increased with compression from 16 kp at 14.6 KN compression to 25 kp at 31.3 KN compression, and corresponding tablet thickness decreased from 7.32±0.3 mm at 14.6 KN to 6.84±0.3 mm at 31.3 KN. Disintegration time increased with compression from about 4:50 min at 14.6 KN compression to about 9:40 min at 31.3 KN. A measure of the dissolution rate showed that at 30 minutes, between about 85% to about 93% of the compound of formula (I-X) was released, and between about 94% and about 99% of the metformin hydrochloride was released.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A pharmaceutical composition comprising
   (a) metformin or a pharmaceutically acceptable salt thereof in an amount in the range of from about 500 mg to about 2000 mg; and
   (b) a compound of formula (I)

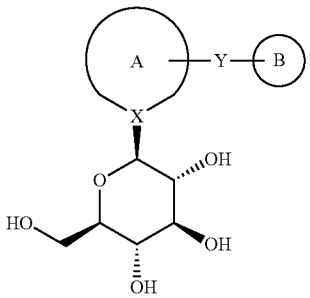

(I)

wherein
Ring A is

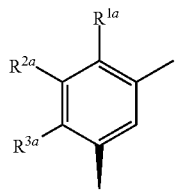

wherein $R^{1a}$ is a halogen atom, a lower alkyl group, or a lower alkoxy group, and $R^{2a}$ and $R^{3a}$ are hydrogen atoms;
and Ring B is

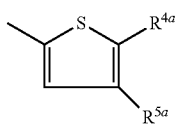

wherein $R^{4a}$ is a phenyl group optionally substituted by a substituent selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and Rya is a hydrogen atom; and Y is —$CH_2$—, or a pharmaceutically acceptable salt thereof; in an amount of from about 10 mg to about 300 mg; and between about 5% and about 50% by weight of diluent which is microcrystalline cellulose;

between about 1% and about 10% by weight of binder comprising a material selected from the group consisting of polyvinylpyrrolidone, methylcellulose, hydroxypropyl cellulose, and hydroxypropyl methylcellulose; and between about 1% and about 10% by weight of disintegrant which is croscarmellose sodium.

2. The pharmaceutical composition as in claim 1, wherein the metformin or pharmaceutically acceptable salt thereof is metformin hydrochloride.

3. A pharmaceutical composition comprising
   (a) metformin hydrochloride in an amount in the range of from about 100 mg to about 2000 mg;
   (b) a compound of formula (I-X)

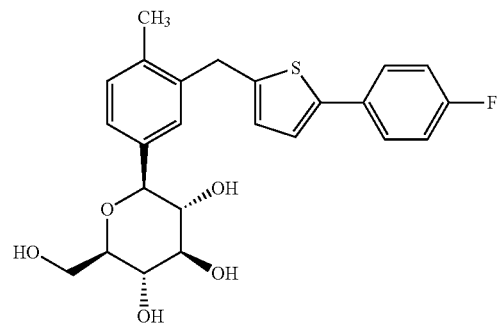

(I-X)

or a pharmaceutically acceptable salt thereof in an amount in the range of from about 50 mg to about 500 mg; and
   (c) between about 5% and about 50% by weight of diluent which is microcrystalline cellulose;
   (d) between about 1% and about 10% by weight of binder comprising a material selected from the group consisting of polyvinylpyrrolidone, methylcellulose, hydroxypropyl cellulose, and hydroxypropyl methylcellulose, and
   (e) between about 1% and about 10% by weight of disintegrant which is croscarmellose sodium.

4. The pharmaceutical composition as in claim 3, wherein the metformin hydrochloride is present in an amount of about 250 mg, about 500 mg, about 750 mg, about 850 mg, or about 1000 mg; and wherein the compound of formula (I-X) or pharmaceutically acceptable salt thereof is present in an amount of about 50 mg, about 100 mg, about 150 mg or about 300 mg.

5. The pharmaceutical composition as in claim 3, wherein the compound of formula (I-X) is a crystalline hemihydrate.

6. The pharmaceutical composition as in claim 3, wherein the metformin hydrochloride is present in an amount of about 500 mg and wherein the compound of formula (I-X) or pharmaceutically acceptable salt thereof is present in an amount of about 50 mg.

7. The pharmaceutical composition as in claim 3, wherein the metformin hydrochloride is present in an amount of about 1000 mg and wherein the compound of formula (I-X) or pharmaceutically acceptable salt thereof is present in an amount of about 50 mg.

8. The pharmaceutical composition as in claim 3, wherein the metformin hydrochloride is present in an amount of about 500 mg and wherein the compound of formula (I-X) or pharmaceutically acceptable salt thereof is present in an amount of about 150 mg.

9. The pharmaceutical composition as in claim 3, wherein the metformin hydrochloride is present in an amount of about 1000 mg and wherein the compound of formula (I-X) or pharmaceutically acceptable salt thereof is present in an amount of about 150 mg.

10. The pharmaceutical composition as in claim 3, wherein the metformin hydrochloride is present in an amount of about 850 mg and wherein the compound of formula (I-X) or pharmaceutically acceptable salt thereof is present in an amount of about 50 mg.

11. The pharmaceutical composition as in claim 3, wherein the metformin hydrochloride is present in an amount of about 850 mg and wherein the compound of formula (I-X) or pharmaceutically acceptable salt thereof is present in an amount of about 50 mg.

12. The pharmaceutical composition as in claim 3, further comprising between about 0.1% and about 2% by weight of a lubricant.

* * * * *